US012745988B2

(12) United States Patent
Watanabe et al.

(10) Patent No.: US 12,745,988 B2
(45) Date of Patent: Sep. 29, 2026

(54) ULTRASONIC DIAGNOSIS APPARATUS, IMAGE PROCESSING APPARATUS, AND IMAGE PROCESSING METHOD FOR TISSUE DISPLACEMENT CAUSED BY A SHEARWAVE GENERATED BY ACOUSTIC RADIATION FORCE

(71) Applicant: Canon Kabushiki Kaisha, Tokyo (JP)

(72) Inventors: Masaki Watanabe, Shioya (JP); Yuko Kanayama, Nasushiobara (JP); Tetsuya Kawagishi, Nasushiobara (JP); Yoshimi Muto, Nasushiobara (JP); Eiji Goto, Utsunomiya (JP); Koichiro Kurita, Nasushiobara (JP); Shogo Fukuda, Otawara (JP)

(73) Assignee: Canon Kabushiki Kaisha, Tokyo (JP)

( * ) Notice: Subject to any disclaimer, the term of this patent is extended or adjusted under 35 U.S.C. 154(b) by 643 days.

(21) Appl. No.: 17/992,055

(22) Filed: Nov. 22, 2022

(65) Prior Publication Data

US 2023/0080726 A1 Mar. 16, 2023

Related U.S. Application Data

(62) Division of application No. 14/568,560, filed on Dec. 12, 2014, now Pat. No. 11,534,142.

(30) Foreign Application Priority Data

Dec. 13, 2013 (JP) ................................ 2013-258666

(51) Int. Cl.

| | |
|---|---|
| ***A61B 8/00*** | (2006.01) |
| ***A61B 8/08*** | (2006.01) |
| ***G01S 7/52*** | (2006.01) |

(52) U.S. Cl.

CPC .......... *A61B 8/5253* (2013.01); *A61B 8/0833* (2013.01); *A61B 8/463* (2013.01);

(Continued)

(58) Field of Classification Search

CPC ..... A61B 8/5253; A61B 8/0833; A61B 8/463; A61B 8/469; A61B 8/485; A61B 8/5207; A61B 8/5246; A61B 8/488; G01S 7/52022

See application file for complete search history.

(56) References Cited

U.S. PATENT DOCUMENTS

| | | | |
|---|---|---|---|
| 6,419,632 | B1 | 7/2002 | Shiki |
| 8,081,806 | B2 | 12/2011 | Friedman |

(Continued)

FOREIGN PATENT DOCUMENTS

| | | | |
|---|---|---|---|
| JP | 2013-000349 | A | 1/2013 |
| JP | 2013-523325 | A | 6/2013 |

OTHER PUBLICATIONS

Thomas Deffieux et al. "On the Effects of Reflected Waves in Transient Shear Wave Elastography", IEEE Transactions on Ultrasonics, Ferroelectrics, and Frequency Control, vol. 58, No. 10, 2011, 4 pages.

(Continued)

*Primary Examiner* — Serkan Akar

(74) *Attorney, Agent, or Firm* — Oblon, McClelland, Maier & Neustadt, L.L.P.

(57) ABSTRACT

An ultrasonic diagnosis apparatus according to an embodiment includes a transmission unit, a reception unit, a generator, and a display controller. The transmission unit causes an ultrasonic probe to transmit a displacement-producing ultrasonic wave and causes the probe to transmit a displacement-observing ultrasonic wave. The reception unit generates reflected-wave data based on a reflected wave received (Continued)

by the probe. The generator calculates displacement at each of a plurality of positions in the scan area over a plurality of time phases, based on the reflected-wave data, determines a time phase when the calculated displacement is substantially maximum, for each of the positions, and generates image data representing positions where the determined time phases are substantially the same as each other, among the positions. The display controller superimposes an image based on the image data on a medical image corresponding to an area including the scan area.

19 Claims, 21 Drawing Sheets

(52) U.S. Cl.
CPC .............. *A61B 8/469* (2013.01); *A61B 8/485* (2013.01); *A61B 8/5207* (2013.01); *A61B 8/5246* (2013.01); *G01S 7/52022* (2013.01); *A61B 8/488* (2013.01)

(56) References Cited

U.S. PATENT DOCUMENTS

| | | | | |
|---|---|---|---|---|
| 2004/0006270 | A1 | 1/2004 | Jeong | |
| 2011/0077518 | A1* | 3/2011 | Miyachi | A61B 5/02007 600/443 |
| 2013/0102932 | A1 | 4/2013 | Cain | |
| 2014/0046173 | A1 | 2/2014 | Greenleaf | |
| 2014/0276046 | A1 | 9/2014 | Kim | |
| 2015/0150535 | A1 | 6/2015 | Fan | |

OTHER PUBLICATIONS

Office Action issued on Sep. 4, 2018 in Japanese Patent Application No. 2014-242206.

McLaughlin et al., "Shear Wave Speed Recovery in Transient Elastography and Supersonic Imaging Using Propagating Fronts", Inverse Problems 22 (2006) 681-706.

* cited by examiner

ULTRASONIC DIAGNOSIS APPARATUS, IMAGE PROCESSING APPARATUS, AND IMAGE PROCESSING METHOD FOR TISSUE DISPLACEMENT CAUSED BY A SHEARWAVE GENERATED BY ACOUSTIC RADIATION FORCE

CROSS-REFERENCE TO RELATED APPLICATIONS

This application is a divisional of and claims benefit under 35 U.S.C. § 120 to U.S. application Ser. No. 14/568,560, filed on Dec. 12, 2014, which is based upon and claims the benefit of priority under 35 U.S.C. § 119 to Japanese Patent Application No. 2013-258666, filed on Dec. 13, 2013, the entire contents of each of which are incorporated herein by reference.

FIELD

Embodiments described herein relate generally to an ultrasonic diagnosis apparatus, an image processing apparatus, and an image processing method.

BACKGROUND

Elastography is conventionally known, in which stiffness of living tissue is measured and the distribution of the measured stiffness is visualized. Elastography is utilized, for example, for diagnosis of diseases such as liver cirrhosis with which the stiffness of living tissue changes with the progress of lesions. In elastography, the method of evaluating stiffness by displacing living tissue is roughly classified into either of the following two types.

The method of the first type visualizes relative stiffness from the magnitude of strain at each point in a scanned section observed when living tissue is pressed and released from the body surface with an ultrasonic probe. The method of the second type obtains an elastic modulus by obtaining the propagation speed of a shear wave by applying acoustic radiation force or mechanical vibration to living tissue from the body surface to produce displacement caused by a shear wave and observing the displacement at each point in a scanned section over time. In the former method, the local magnitude of strain depends on the magnitude of manually moving the ultrasonic probe and whether the region of interest is hard or soft relatively to the surroundings is evaluated. By contrast, in the latter method, the absolute elastic modulus of the region of interest can be obtained.

The stiffness of living tissue may not be measured accurately, for example, when displacement is caused by the subject's body movement or when the shear wave is reflected or refracted in tissue. In such a case, the stiffness image visualized by elastography is less reliable.

DETAILED DESCRIPTION

An ultrasonic diagnosis apparatus according to an embodiment includes a transmission unit, a reception unit, an image generator, and a display controller. The transmission unit causes an ultrasonic probe to transmit a displacement-producing ultrasonic wave for producing displacement in living tissue based on acoustic radiation force and causes the ultrasonic probe to transmit an observation ultrasonic wave for observing displacement, in living tissue in a predetermined scan area, that is produced based on the displacement-producing ultrasonic wave. The reception unit generates reflected-wave data based on a reflected wave received by the ultrasonic probe. The image generator calculates displacement at each of a plurality of positions in the scan area over a plurality of time phases, based on the reflected-wave data, determines a time phase when the calculated displacement is substantially maximum, for each of the positions, and generates image data representing positions where the determined time phases are substantially the same as each other, among the positions. The display controller superimposes an image based on the image data on a medical image corresponding to an area including the scan area.

An ultrasonic diagnosis apparatus, an image processing apparatus, and an image processing method according to embodiments are described below with reference to the drawings.

First Embodiment

Figure 1:
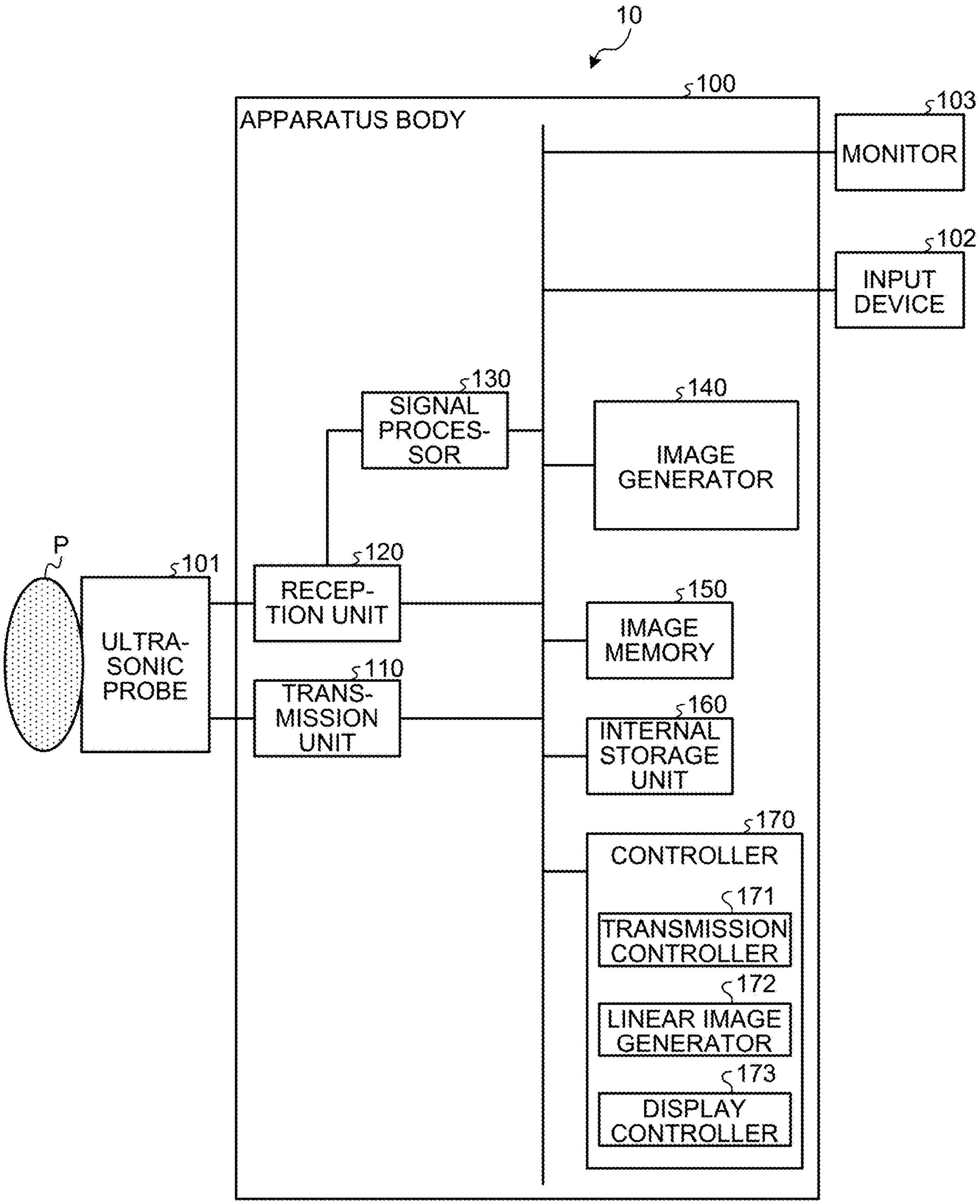
FIG. 1 is a block diagram illustrating a configuration example of an ultrasonic diagnosis apparatus according to a first embodiment.

First, a configuration of the ultrasonic diagnosis apparatus according to a first embodiment is described. FIG. 1 is a block diagram illustrating a configuration example of the ultrasonic diagnosis apparatus according to the first embodiment. As illustrated in FIG. 1, an ultrasonic diagnosis apparatus 10 according to the first embodiment includes an apparatus body 100, an ultrasonic probe 101, an input device 102, and a monitor 103.

The ultrasonic probe 101 includes a plurality of transducer elements (for example, piezoelectric transducer elements). The transducer elements produce an ultrasonic wave based on a drive signal supplied from a transmission unit 110 of the apparatus body 100 described later. The transducer elements of the ultrasonic probe 101 receive a reflected wave from a subject P and convert the received reflected wave into an electrical signal. The ultrasonic probe 101 additionally includes a matching layer provided to the transducer elements and a backing material for preventing propagation of ultrasonic waves backward of the transducer elements.

When an ultrasonic wave is transmitted from the ultrasonic probe 101 to the subject P, the transmitted ultrasonic wave is successively reflected on an acoustic impedance discontinuous surface in living tissue of the subject P and received as a reflected-wave signal by the transducer elements of the ultrasonic probe 101. The amplitude of the received reflected-wave signal depends on the difference of acoustic impedance on the discontinuous surface on which the ultrasonic wave is reflected. In a case where the transmitted ultrasonic pulse is reflected at the moving blood flow or a surface such as the heart wall, the reflected-wave signal undergoes a frequency shift due to the Doppler effect, depending on the velocity component of the moving body relative to the ultrasound transmission direction.

It is noted that the first embodiment is applicable to the ultrasonic probe 101 illustrated in FIG. 1 of any type, including a one-dimensional ultrasonic probe having piezoelectric transducer elements arranged in a row, a one-dimensional ultrasonic probe having piezoelectric transducer elements arranged in a row and mechanically swung, and a two-dimensional ultrasonic probe having piezoelectric transducer elements two-dimensionally arranged in a grid pattern.

The input device 102 includes a mouse, a keyboard, a button, a panel switch, a touch command screen, a footswitch, a trackball, and a joystick for accepting a variety of setting requests from the operator of the ultrasonic diagnosis apparatus 10 and transferring the accepted setting requests to the apparatus body 100.

The monitor 103 displays a graphical user interface (GUI) for the operator of the ultrasonic diagnosis apparatus 10 to input a variety of setting requests using the input device 102 and displays ultrasonic image data or other data generated in the apparatus body 100.

The apparatus body 100 is a device that generates ultrasonic image data based on the reflected-wave signal received by the ultrasonic probe 101 and includes the transmission unit 110, a reception unit 120, a signal processor 130, an image generator 140, an image memory 150, an internal storage unit 160, and a controller 170, as illustrated in FIG. 1.

The transmission unit 110 controls transmission directivity in ultrasound transmission. Specifically, the transmission unit 110 includes a rate pulse generator, a transmission delay unit, and a transmission pulser to supply a drive signal to the ultrasonic probe 101. The rate pulser generator repeatedly generates, at a predetermined rate frequency (pulse repetition frequency (PRF)), rate pulses for forming ultrasonic waves to be transmitted. With the rate pulses passed through the transmission delay unit to have different transmission delays, voltage is applied to the transmission pulser. That is, the transmission delay unit provides necessary transmission delays for the respective transducer elements to individual rate pulses generated by the rate pulser, in order to concentrate ultrasonic waves generated from the ultrasonic probe 101 into a beam and fix the transmission directivity. The transmission pulser applies a drive signal (drive pulse) to the ultrasonic probe 101 at a timing based on such a rate pulse. The transmission direction or the transmission delays is stored in the internal storage unit 160 described later and the transmission unit 110 refers to the internal storage unit 160 to control the transmission directivity.

The drive pulse is transmitted from the transmission pulser through a cable to the transducer element in the ultrasonic probe 101 and thereafter converted from an electrical signal to mechanical vibration in the transducer elements. The mechanical vibration is transmitted as an ultrasonic wave in the inside of the living body. The ultrasonic waves having transmission delays different among transducer elements converge and propagate in a predetermined direction. The transmission delay unit adjusts the transmission direction from the transducer element surfaces as desired by changing the transmission delays provided to individual rate pulses. The transmission unit 110 provides transmission directivity by controlling the number and positions (transmission aperture) of transducer elements for use in transmission of ultrasonic beams and the transmission delays corresponding to the positions of the respective transducer elements that constitute the transmission aperture. For example, the transmission delay circuit in the transmission unit 110 controls the position of the convergence point (transmission focus) in the depth direction of ultrasound transmission by providing transmission delays to individual rate pulses generated by the pulser circuit.

The transmission unit 110 has a function capable of instantaneously changing a transmission frequency, a transmission drive voltage, and the like for executing a predetermined scan sequence, based on an instruction from the controller 170 described later. In particular, the transmission drive voltage is changed by a linear-amplifier type oscillator circuit capable of instantaneously changing its value or a mechanism for electrically switching a plurality of power supply units.

The reflected wave of the ultrasonic wave transmitted by the ultrasonic probe 101 reaches the transducer elements in the ultrasonic probe 101 and is then converted from mechanical vibration into an electrical signal (reflected-wave signal) for input to the reception unit 120.

The reception unit 120 controls reception directivity in ultrasound reception. Specifically, the reception unit 120 includes a pre-amplifier, an analog/digital (A/D) converter, a reception delay unit, and an adder, and performs a variety of processing on the reflected-wave signal received by the ultrasonic probe 101 to generate reflected-wave data. The pre-amplifier performs gain correction by amplifying the reflected-wave signal for each channel. The A/D converter converts the reflected-wave signal having the gain corrected from analog to digital. The reception delay unit provides a reception delay necessary to determine reception directivity for each channel. The adder generates reflected-wave data by adding the reflected-wave signals (digital signals) having the reception delays. The adding processing by the adder enhances a reflection component from the direction corresponding to the reception directivity of the reflected-wave signal. The reception direction or the reception delay is stored in the internal storage unit 160 described later and the reception unit 120 refers to the internal storage unit 160 to control the reception directivity. It is noted that the reception unit 120 according to the first embodiment is capable of parallel simultaneous reception.

The signal processor 130 performs a variety of signal processing on the reflected-wave data generated by the reception unit 120 from the reflected-wave signal. The signal processor 130 generates data (B mode data) representing the signal intensity for each sample point (observation point) by brightness of luminance by performing logarithmic amplification, envelope detection, or other processing on the reflected-wave data received from the reception unit 120.

The signal processor 130 generates, from the reflected-wave data received from the reception unit 120, data (Doppler data) in which movement information of a moving body based on the Doppler effect is extracted for each sample point in a scan area. Specifically, the signal processor 130 generates Doppler data in which the average velocity, the variance, the power value, or the like is extracted as the movement information of the moving body for each sample point. Here, the moving body is, for example, blood flow, tissue of the heart wall or other parts, or a contrast medium.

Here, the ultrasonic diagnosis apparatus 10 according to the first embodiment is a device capable of elastography for measuring the stiffness of living tissue and imaging the distribution of the measured stiffness. Specifically, the ultrasonic diagnosis apparatus 10 according to the first embodiment is a device capable of elastography by applying acoustic radiation force to produce displacement in living tissue.

That is, the transmission unit 110 according to the first embodiment causes the ultrasonic probe 101 to transmit a push pulse (displacement-producing burst wave) for producing displacement caused by a shear wave generated by acoustic radiation force. The transmission unit 110 according to the first embodiment then causes the ultrasonic probe 101 to transmit an observation pulse for observing displacement produced by the push pulse, multiple times for each of a plurality of scan lines in the scan area. The observation pulse is transmitted in order to observe the propagation speed of the shear wave produced by the push pulse for each sample point in the scan area. In general, the observation pulse is transmitted multiple times (for example, a hundred times) for each scan line in the scan area. The reception unit 120 generates reflected-wave data from the reflected-wave signal of the observation pulse transmitted for each scan line in the scan area. It is noted that the push pulse is an example of the displacement-producing ultrasonic wave. The observation pulse is an example of the observation ultrasonic wave.

In other words, the transmission unit 110 causes an ultrasonic probe to transmit a displacement-producing ultrasonic wave for producing displacement in living tissue based on acoustic radiation force and causes the ultrasonic probe to transmit an observation ultrasonic wave for observing displacement that is produced in living tissue in a predetermined scan area based on the displacement-producing ultrasonic wave. The reception unit 120 generates reflected-wave data based on the reflected wave received by the ultrasonic probe.

The signal processor 130 calculates stiffness distribution information indicating the distribution of stiffness in the scan area by analyzing the reflected-wave data of the observation pulses transmitted multiple times for each scan line in the scan area. Specifically, the signal processor 130 generates stiffness distribution information of the scan area by measuring the propagation speed of the shear wave produced by the push pulse at each sample point.

For example, the signal processor 130 analyzes the frequency of the reflected-wave data of the observation pulse. The signal processor 130 thus generates movement information (tissue Doppler data) at each of a plurality of sample points on each scan line over a plurality of time phases. The signal processor 130 then performs time-integration of the velocity components of the tissue Doppler data over a plurality of time phases obtained for each of a plurality of sample points on each scan line. The signal processor 130 thus calculates displacement at each of a plurality of sample points on each scan line over a plurality of time phases. The signal processor 130 then obtains the time when displacement is maximum at each sample point. The signal processor 130 then determines that the time when the maximum displacement is reached at each sample point is the arrival time when the shear wave reaches each sample point. Subsequently, the signal processor 130 calculates the propagation speed of the shear wave at each sample point by performing spatial differentiation of the arrival time of the shear wave at each sample point. The "propagation speed of the shear wave" is hereinafter referred to as "shear wave speed". The arrival time used may not be the time when displacement is maximum at each sample point but may be, for example, the time when the amount of change of displacement at each sample point is maximum.

The signal processor 130 then generates stiffness distribution information by color-coding the shear wave speeds and mapping the color-coded shear wave speeds to the corresponding sample points. While the shear wave speed is high in hard tissue, the shear wave speed is low in soft tissue. That is, the value of the shear wave speed indicates the stiffness (elastic modulus) of tissue. In the case described above, the observation pulse is a transmission pulse for tissue Doppler. The shear wave speed may not be based on the time (arrival time) when displacement is maximum at each sample point but may be, for example, calculated through detection by the signal processor 130 by cross-correlation of displacement of tissue on adjacent scan lines.

The signal processor 130 may calculate the Young's modulus or the shear modulus from the shear wave speed and generate stiffness distribution information from the calculated Young's modulus or shear modulus. Any one of the shear wave speed, the Young's modulus, and the shear modulus can be used as a physical quantity (index value) representing the stiffness of living tissue. In the following description, the signal processor 130 uses the Young's modulus as a physical quantity representing the stiffness of living tissue.

Here, the shear wave produced by one-time transmission of a push pulse attenuates while propagating. When the shear wave speed is intended to be observed over a wide area, the shear wave produced by a push pulse transmitted on one particular scan line attenuates while propagating and finally becomes unable to be observed when it is sufficiently away from the transmission position of the push pulse.

In such a case, it is necessary to transmit a push pulse at a plurality of positions in the orientation direction. Specifically, the scan area (or the region of interest) is divided into a plurality of areas along the orientation direction. The transmission unit 110 transmits a push pulse at different scan line positions to produce a shear wave before the observation pulse is transmitted and received in each divided area (hereinafter denoted as a divided area). In doing so, the transmission position of a push pulse is typically set in the vicinity of each divided area. When the number of signals that are simultaneously received in parallel is limited to a small number, the transmission unit 110 successively executes a process of transmitting the observation pulse multiple times on each scan line in a divided area after transmitting the push pulse once for each of the divided areas.

The image generator 140 generates ultrasonic image data from the data generated by the signal processor 130. The image generator 140 generates B mode image data representing the intensity of the reflected wave by brightness, from the B mode data generated by the signal processor 130. The image generator 140 also generates Doppler image data representing moving-body information from the Doppler data generated by the signal processor 130. The Doppler image data is velocity image data, variance image data, power image data, or image data formed of a combination thereof.

The image generator 140 also generates stiffness image data representing the stiffness of living tissue by color, from the stiffness distribution information generated by the signal processor 130. For example, the image generator 140 generates, as stiffness image data, shear wave speed image data in which a pixel value corresponding to the shear wave speed at each point (each sample point) in the scan area is assigned to the point.

Figure 2:
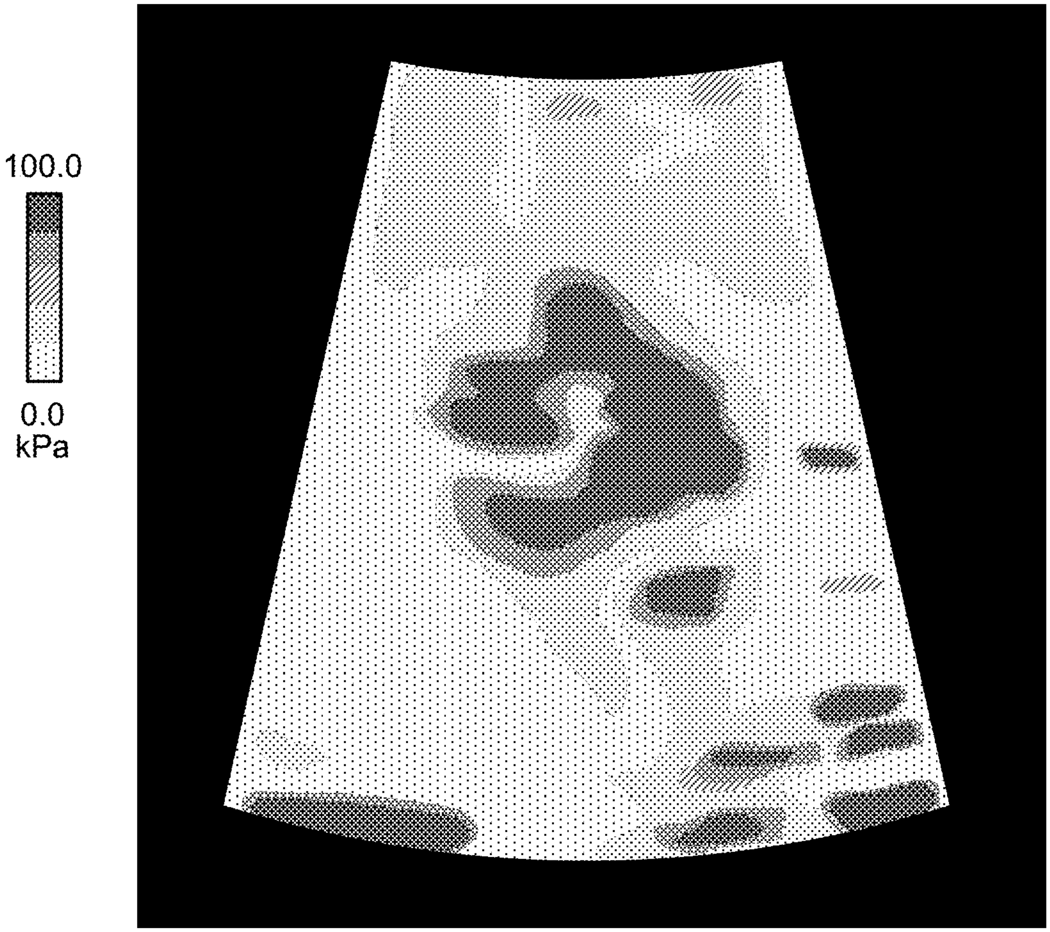
FIG. 2 is a diagram illustrating an example of stiffness image data according to the first embodiment.

FIG. 2 is a diagram illustrating an example of the stiffness image data according to the first embodiment. As illustrated in FIG. 2, the image generator 140 generates a color-coded image of the stiffness of living tissue. FIG. 2 illustrates a case where the entire scan area is designated as a target to be imaged by elastography, for convenience of explanation. However, the embodiments are not limited to this case. For example, when a region of interest (ROI) that is part of the scan area is designated as a target to be imaged, stiffness image data corresponding to the ROI is generated. In the first embodiment, the ROI corresponds to a target area to be imaged by elastography.

Here, the image generator 140, in general, generates display ultrasonic image data by scan-converting a scan line signal sequence of ultrasonic scan into a scan line signal sequence in a video format typically of televisions. Specifically, the image generator 140 generates display ultrasonic image data by performing coordinate transformation in accordance with the mode of ultrasonic scan with the ultrasonic probe 101. The image generator 140 also performs a variety of image processing other than scan conversion, for example, such as image processing (smoothing processing) of reproducing a brightness mean value image using a plurality of image frames after scan conversion and image processing (edge enhancement) using a differential filter in an image. The image generator 140 also combines supplemental information (such as character information of various parameters, scales, and body marks) with ultrasonic image data.

That is, B mode data, Doppler data, and stiffness distribution information are ultrasonic image data before the scan conversion processing, and the data generated by the image generator 140 is display ultrasonic image data after the scan conversion processing. When the signal processor 130 generates three-dimensional data (three-dimensional B mode data, three-dimensional Doppler data, and three-dimensional stiffness distribution information), the image generator 140 generates volume data by performing coordinate transformation in accordance with the mode of ultrasonic scan with the ultrasonic probe 101. The image generator 140 then generates two-dimensional image data for display by performing a variety of rendering processing on the volume data.

The image memory 150 is a memory for storing display image data generated by the image generator 140. The image memory 150 may also store data generated by the signal processor 130. The B mode data, the Doppler data, or the stiffness distribution information stored in the image memory 150 can be invoked by the operator, for example, after diagnosis, and is turned into display ultrasonic image data through the image generator 140.

The internal storage unit 160 stores a variety of data such as control programs for ultrasound transmission and reception, image processing and display processing, diagnosis information (for example, such as patient ID and doctor's opinion), diagnosis protocols, and a variety of body marks. The internal storage unit 160 is also used for retaining image data stored by the image memory 150, as necessary. The data stored in the internal storage unit 160 can be transferred to an external device through an interface (not illustrated).

The internal storage unit 160 also stores information about the already captured shear wave speed image data. For example, the internal storage unit 160 stores the arrival time of the shear wave at each sample point, for the captured shear wave speed image data.

The controller 170 controls the entire processing in the ultrasonic diagnosis apparatus 10. Specifically, the controller 170 controls the processes in the transmission unit 110, the reception unit 120, the signal processor 130, and the image generator 140, based on a variety of setting requests input from the operator through the input device 102, and a variety of control programs and a variety of data read from the internal storage unit 160. The controller 170 performs control such that the display ultrasonic image data stored in the image memory 150 appears on the monitor 103.

The transmission unit 110, the reception unit 120, the controller 170, and others contained in the apparatus body 100 may be configured with hardware of a processor (such as a central processing unit (CPU), a micro-processing unit (MPU), or an integrated circuit) or may be configured with computer programs organized into modules in a software product.

The stiffness of living tissue may not be accurately measured, for example, when displacement is produced by the subject's body movement or when the shear wave is reflected and refracted in tissue. In such a case, the stiffness image visualized by elastography is less reliable.

The ultrasonic diagnosis apparatus 10 according to the first embodiment can represent the reliability of the stiffness image on the stiffness image. The configuration of the ultrasonic diagnosis apparatus 10 for implementing this function is described below.

In the ultrasonic diagnosis apparatus 10 according to the first embodiment, the controller 170 includes a transmission controller 171, a linear image generator 172, and a display controller 173.

The transmission controller 171 controls transmission of a push pulse and transmission and reception of an observation pulse by the transmission unit 110. For example, the transmission controller 171 accepts an instruction to determine an ROI from the operator. The transmission controller 171 then sets, for example, the transmission position of a push pulse, the number of transmission positions, the position of the ROI, the range of the ROI, and the number of ROIs for generating stiffness image data corresponding to the ROI, based on the accepted instruction. The transmission unit 110 causes the ultrasonic probe 101 to transmit a push pulse under the control of the transmission controller 171. The transmission unit 110 also causes the ultrasonic probe 101 to transmit an observation pulse for observing displacement produced by the transmitted push pulse, multiple times for each of a plurality of scan lines in the scan area, under the control of the transmission controller 171.

The linear image generator 172 generates linear image data representing a line on which the arrival times when the shear wave reaches individual points in the scan area are substantially the same as each other. This linear image data is information, for example, for displaying a contour line that connects the positions where the arrival times are substantially the same as each other. For example, the linear image generator 172 extracts a plurality of points having a predetermined arrival time from the points (sample points) in the scan area. The linear image generator 172 then generates linear image data by connecting the extracted points. The predetermined arrival time is a value designated beforehand by the operator or the designer of the ultrasonic diagnosis apparatus 10, and a plurality of values are usually designated. The linear image generator 172 is an example of the arrival time image generator or the image generator.

In other words, the linear image generator 172 calculates displacement at each of a plurality of positions in the scan area over a plurality of time phases, based on the reflected-wave data, determines the time phase when the calculated displacement is substantially maximum, for each of the positions, and generates image data representing positions where the determined time phases are substantially the same as each other, among the positions. Specifically, the linear image generator 172 generates the image data corresponding to a plurality of discrete time phases.

Figure 3:
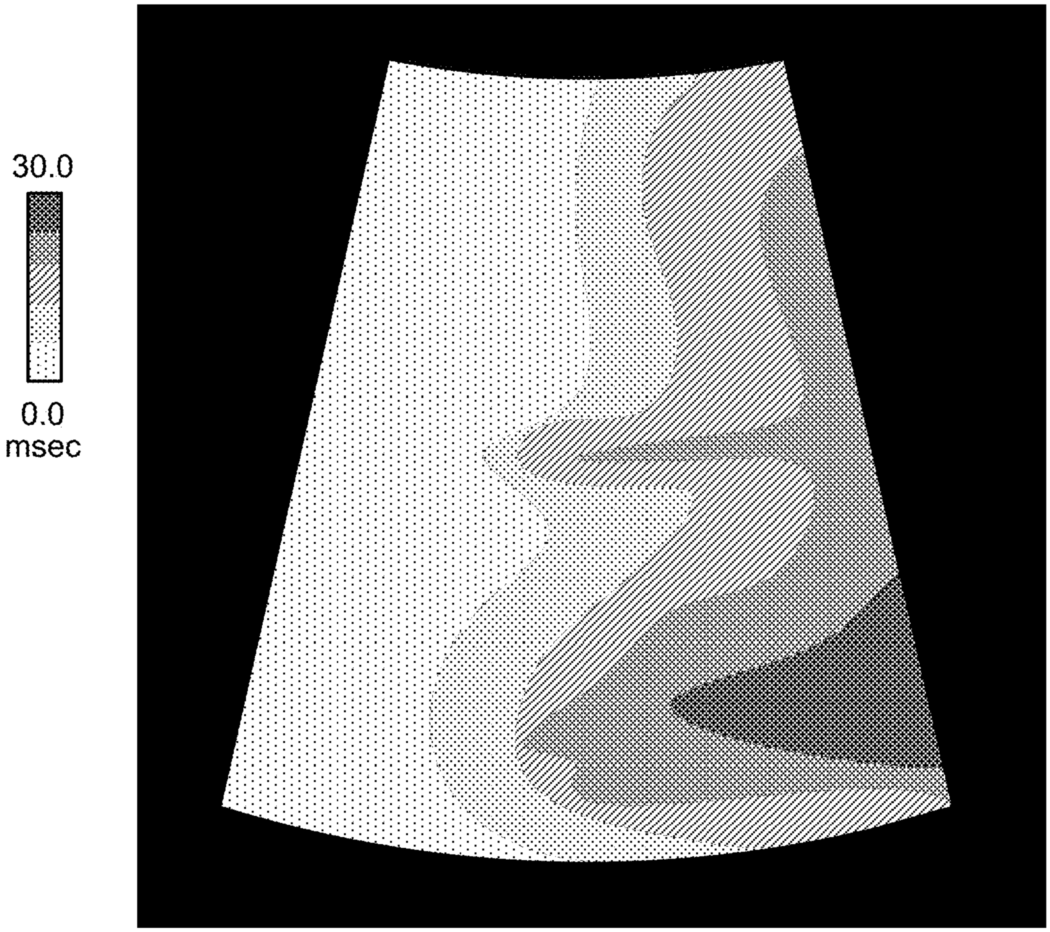
FIG. 3 is a diagram for explaining a process to be performed by a linear image generator according to the first embodiment.
Figure 4:
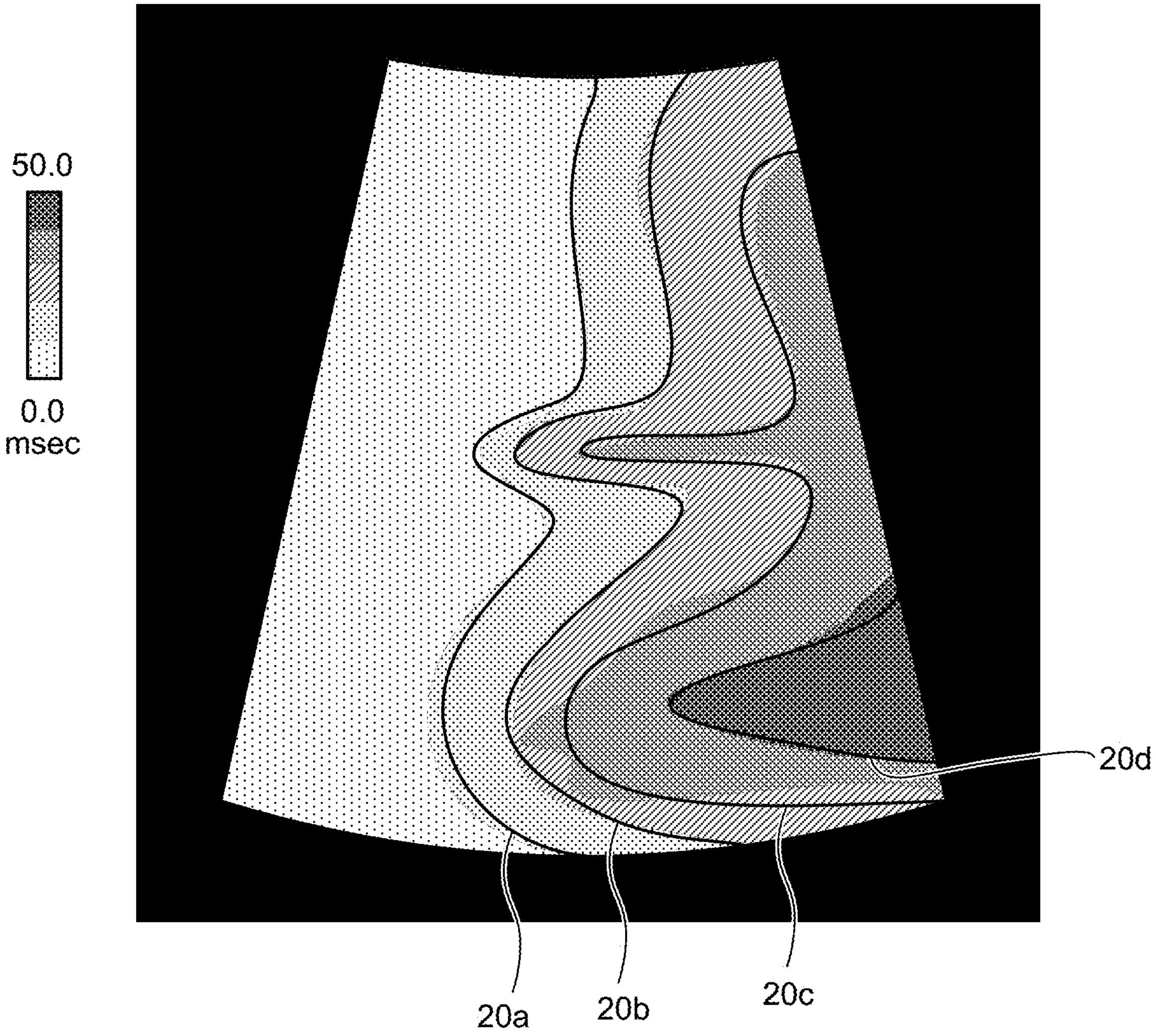
FIG. 4 is a diagram for explaining the process to be performed by the linear image generator according to the first embodiment.

FIG. 3 and FIG. 4 are diagrams for explaining a process performed by the linear image generator 172 according to the first embodiment. FIG. 3 illustrates an example of the arrival time image data in which a pixel value corresponding to the arrival time at each point is assigned to the point in the scan area. FIG. 4 illustrates a case where linear image data 20*a*, 20*b*, 20*c*, 20*d* generated by the linear image generator 172 is displayed on the arrival time image data in FIG. 3. The linear image data 20*a* represents positions where the arrival time is 10 [msec], the linear image data 20*b* represents positions where the arrival time is 20 [msec], the linear image data 20*c* represents positions where the arrival time is 30 [msec], and the linear image data 20*d* represents positions where the arrival time is 40 [msec]. The linear image data 20*a*, 20*b*, 20*c*, 20*d* is collectively denoted as "linear image data 20" unless it is necessary to distinguish them from each other. The linear image data 20 is an example of the arrival time position image data.

First, the arrival time image data in FIG. 3 is described. The arrival time image data is generated, for example, by the image generator 140. Specifically, the image generator 140 generates arrival time image data by assigning a pixel value corresponding to the arrival time at each point as determined by the signal processor 130 to the point in the scan area.

The linear image generator 172 then acquires the arrival time image data generated by the image generator 140. The linear image generator 172 then extracts a plurality of points where the arrival time is 10 [msec] from the acquired arrival time image data. The linear image generator 172 then generates linear image data 20*a* by connecting the extracted points. The linear image generator 172 generates linear image data 20*b* by connecting the points of 20 [msec], generates linear image data 20*c* by connecting the points of 30 [msec], and generates linear image data 20*d* by connecting the points of 40 [msec], in the same manner as in the linear image data 20*a*.

The linear image generator 172, for example, assigns a different pixel value corresponding to the arrival time to each piece of the linear image data 20. In the example illustrated in FIG. 4, the linear image generator 172 assigns a different pixel value corresponding to the arrival time to each piece of the linear image data 20*a*, 20*b*, 20*c*, 20*d*. As an example, the linear image generator 172 assigns, to the respective pieces of the linear image data 20*a*, 20*b*, 20*c*, 20*d*, different colors assigned corresponding to the arrival times at the respective points in the arrival time image data in FIG. 3. Specifically, the linear image generator 172 assigns blue to the linear image data 20*a*, assigns green to the linear image data 20*b*, assigns yellow to the linear image data 20*c*, and assigns red to the linear image data 20*d*.

As described above, the linear image generator 172 generates the linear image data 20*a*, 20*b*, 20*c*, and 20*d* representing the positions where the arrival times are 10, 20, 30, and 40 [msec], respectively.

It is noted that FIG. 4 is only an example. For example, in the example in FIG. 4, the linear image data 20 is generated at the positions where the arrival times are 10, 20, 30, and 40 [msec]. However, the embodiments are not limited to this example. For example, the linear image generator 172 may generate linear image data 20 at the position of any arrival time or may generate any number of pieces of linear image data 20.

In the example in FIG. 4, a pixel value corresponding to the arrival time is assigned to each piece of the linear image data 20. However, the embodiments are not limited to this example. For example, the linear image generator 172 may assign different kinds of lines (solid line, dashed line, dotted line, dashed and single-dotted line, and other lines) to pieces of linear image data 20 with different arrival times.

For convenience of explanation, the description here provides the example in which the linear image data 20 is generated after the arrival time image data (FIG. 3) is generated. However, the embodiments are not limited to this example. That is, the linear image generator 172 can generate linear image data 20 even when the arrival time image data is not generated. For example, the linear image generator 172 can generate linear image data 20 by extracting a plurality of points having a predetermined arrival time among the arrival times at individual points as determined by the signal processor 130.

Although not described here, the linear image generator 172 may perform, for example, smoothing processing for smoothing the linear image data 20 or may perform processing for making the thickness of the linear image data 20 uniform when generating linear image data 20. When extracting points having a predetermined arrival time, the linear image generator 172 may perform the extraction, for example, allowing a margin of error to such an extent that the extracted points form a linear shape, rather than extracting only the points that exactly match the predetermined arrival time. That is, the "line on which the arrival times are substantially the same as each other" refers to a line that is based on a plurality of points having the same arrival time within a margin of error to such an extent that the extracted points form a linear shape and that has been subjected to the smoothing processing or the processing for making the thickness uniform.

The display controller 173 superimposes the linear image data on ultrasonic image data. For example, the display controller 173 superimposes the linear image data 20 generated by the linear image generator 172 on stiffness image data.

In other words, the display controller 173 superimposes an image based on the image data generated by the linear image generator 172 on a medical image corresponding to an area including the scan area.

Figure 5:
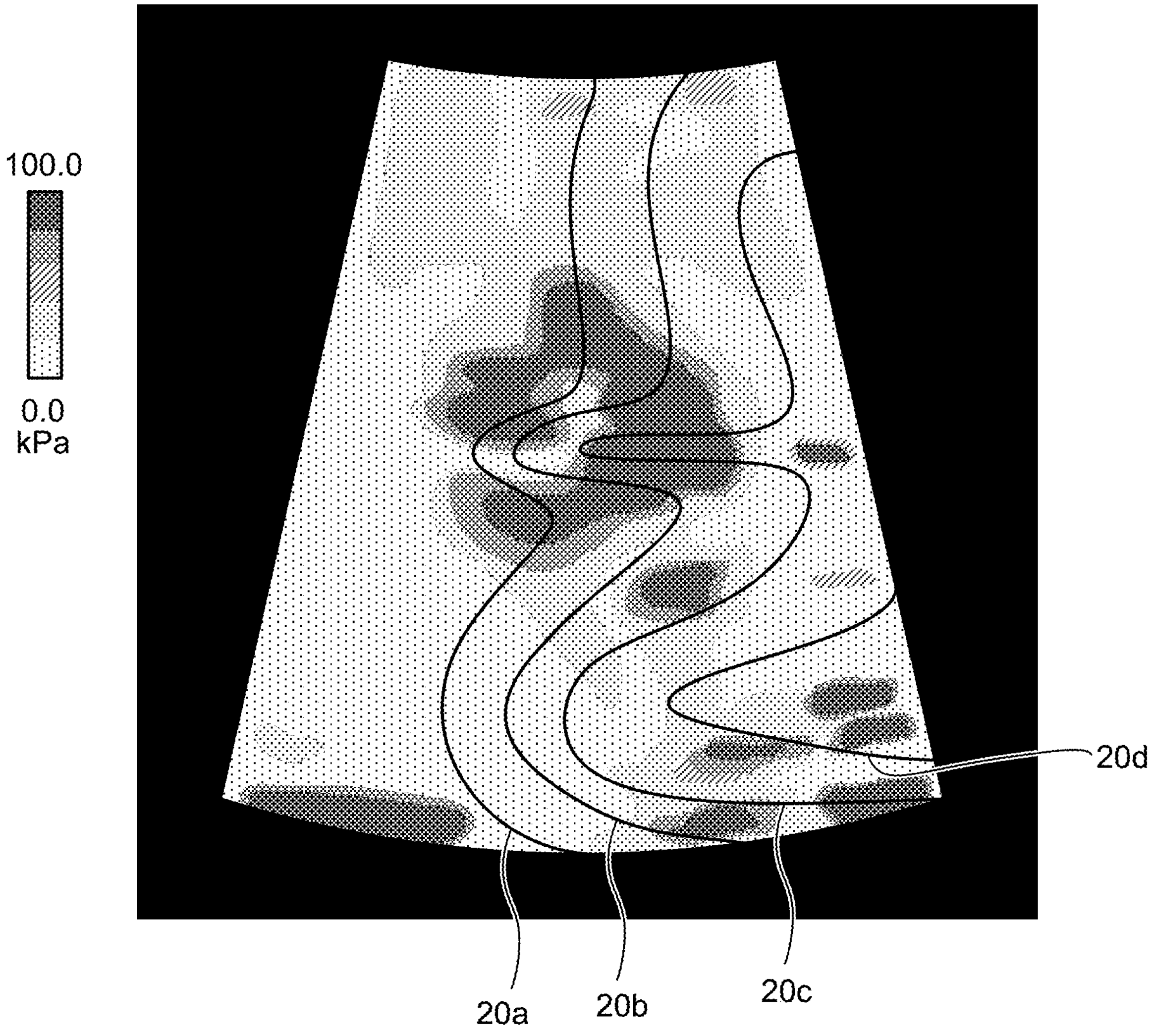
FIG. 5 is a diagram illustrating an example of a display image displayed by a display controller according to the first embodiment.

FIG. 5 is a diagram illustrating an example of a display image displayed by the display controller 173 according to the first embodiment. As illustrated in FIG. 5, the display controller 173 displays the linear image data 20*a*, 20*b*, 20*c*, 20*d* generated as illustrated in FIG. 4 on the stiffness image data illustrated in FIG. 2.

It is noted that FIG. 5 is merely an example. For example, FIG. 5 illustrates a case where the linear image data 20 is superimposed on the stiffness image data used as a background image. However, the background image is not limited to this image data. For example, B mode image data, the arrival time image data in FIG. 3, displacement image data described later, or variance image data described later may be used as a background image.

Figure 6:
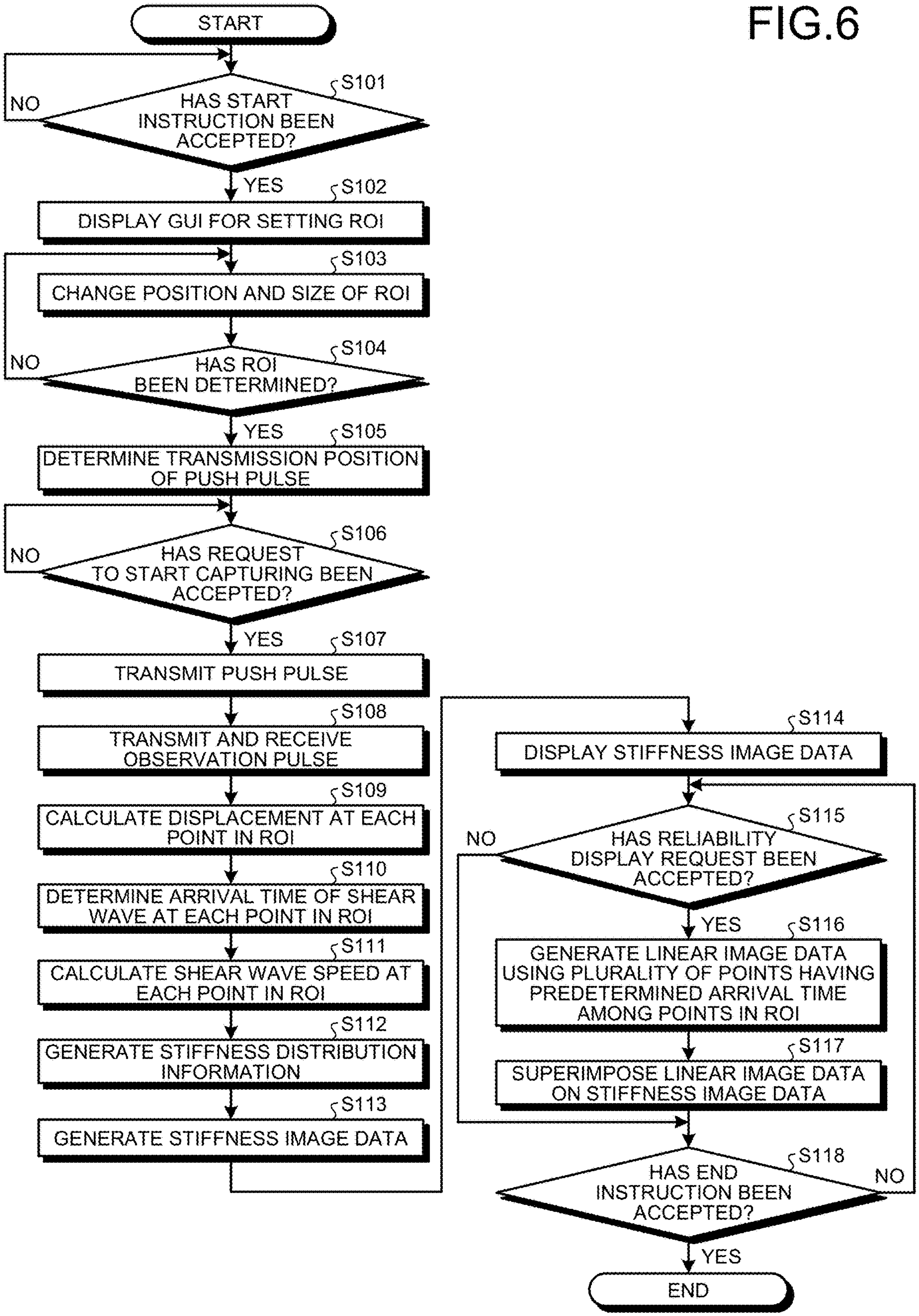
FIG. 6 is a flowchart illustrating an example of the process procedure to be performed in the ultrasonic diagnosis apparatus according to the first embodiment.

FIG. 6 is a flowchart illustrating an example of the process procedure performed by the ultrasonic diagnosis apparatus 10 according to the first embodiment. In the example illustrated in FIG. 6, the ultrasonic diagnosis apparatus 10 is initially set in the B mode and displays B mode image data.

As illustrated in FIG. 6, the transmission controller 171 in the ultrasonic diagnosis apparatus 10 according to the first embodiment determines whether a start instruction to start a stiffness image generation mode for generating a stiffness image has been accepted from the operator (step S101). The stiffness image generation mode is, for example, a state for setting an ROI for generating a stiffness image, and transmitting a push pulse after setting the ROI to generate a stiffness image. If a start instruction has not been accepted (No at step 3101), the transmission controller 171 waits until a start instruction is accepted.

If a start instruction has been accepted (Yes at step 3101), the monitor 103 displays a GUI for setting an ROI under the control of the transmission controller 171 (step S102). As the GUI for setting an ROI, for example, an ROI that specifies a target area to be imaged by elastography is displayed on B mode image data. The position and size of the ROI are preset. The transmission controller 171 then accepts an instruction to change the position and size of the ROI from the operator and changes the position and size of the ROI in accordance with the accepted instruction (step S103).

The transmission controller 171 then determines whether the ROI has been determined (step S104). For example, the transmission controller 171 determines whether the ROI has been determined, depending on whether an instruction to determine the position and size of the ROI has been accepted from the operator. Here, if the ROI has not been determined (No at step S104), the transmission controller 171 executes the processing at step S103 until the ROI is determined.

On the other hand, if the ROI has been determined (Yes at step S104), the transmission controller 171 determines the transmission position of a push pulse based on the determined ROI (step S105). For example, the transmission controller 171 determines one or more transmission positions of a push pulse based on the position and size of the ROI. This processing is performed because a shear wave produced by a push pulse is known to attenuate during the course of propagation, and the purpose thereof is to prevent a situation in which complete scanning of the entire ROI is hindered due to the attenuation.

The transmission controller 171 then determines whether a request to start capturing stiffness image data has been accepted from the operator (step S106). Here, if a request to start capturing has not been accepted (No at step S106), the transmission controller 171 waits until a request to start capturing is accepted.

On the other hand, if a request to start capturing has been accepted (Yes at step S106), the transmission controller 171 causes the ultrasonic probe 101 to transmit a push pulse at the determined transmission position (step S107). The ultrasonic probe 101 then transmits and receives an observation pulse within the ROI, under the control of the transmission unit 110 and the reception unit 120 (step S108). For example, the observation pulse is transmitted and received multiple times (about a hundred times) on a certain scan line in the ROI. The change of displacement over time at each point is thus calculated. With a system capable of receiving multiple signals with a single pulse, the change of displacement over time throughout the entire area in the ROI can be known by transmitting a push pulse once. When the number of signals that are simultaneously received is limited, an observation pulse is transmitted and received multiple times with the raster position changed. In doing so, a push pulse is transmitted every time an observation pulse is transmitted with the raster position changed.

Subsequently, the signal processor 130 calculates displacement at each point in the ROI over a plurality of time phases (step S109). The signal processor 130 then determines the arrival time of the shear wave at each point in the ROI (step S110). For example, the signal processor 130 determines that the time when the maximum displacement is reached at each point is the arrival time of the shear wave at the point. The signal processor 130 then calculates the propagation speed of the shear wave (shear wave speed) at each point by performing spatial differentiation of the arrival time of the shear wave at each point (step S111). The signal processor 130 then generates stiffness distribution information by color-coding the shear wave speeds corresponding to the ROI and mapping the color-coded shear wave speeds to corresponding points (step S112).

Subsequently, the image generator 140 generates stiffness image data representing the stiffness of living tissue by color from the stiffness distribution information generated by the signal processor 130 (step S113). For example, the image generator 140 generates, as the stiffness image data, shear wave speed image data in which a pixel value corresponding to the shear wave speed at each point (each sample point) in the scan area is assigned to the point. The display controller 173 then causes the monitor 103 to display the stiffness image data generated by the image generator 140 (step S114).

The linear image generator 172 determines whether a reliability display request to display reliability has been accepted (step S115). If a reliability display request has been accepted (Yes at step S115), the linear image generator 172 generates linear image data 20 using a plurality of points having a predetermined arrival time among the points in the ROI (step S116). For example, the linear image generator 172 generates linear image data 20 by extracting a plurality of points having a predetermined arrival time from the points in the ROI and connecting the extracted points. The display controller 173 then superimposes the linear image data 20 generated by the linear image generator 172 on the stiffness image data (step S117). If a reliability display request has not been accepted (No at step S115), the process proceeds to step S118.

The transmission controller 171 then determines whether an end instruction to terminate the stiffness image generation mode has been accepted from the operator (step S118). If an end instruction has not been accepted (No at step S118), the transmission controller 171 waits to accept a reliability display request, with the stiffness image data kept displayed, until an end instruction is accepted.

On the other hand, if the transmission controller 171 has accepted an end instruction (Yes at step 3118), the stiffness image generation mode ends. For example, the transmission controller 171 hides the stiffness image data, and the process returns to the B mode.

It is noted that the above process procedure is merely an example, and the embodiments are not limited to the process procedure in FIG. 6. For example, the process of changing the position and size of the ROI (step S103) may not necessarily be executed. For example, if the preset ROI is used as it is, the processing at step S103 may not be executed. For example, in the processing at step S103, only one of the position and the size of the ROI may be changed.

In the process procedure described above, the process of generating linear image data 20 (step S116) is executed after a reliability display request has been accepted (Yes at step S115). However, the embodiments are not limited to this processing. For example, the process of generating linear image data 20 may be executed as a background process, and linear image data 20 may be displayed if a reliability display request is accepted. That is, the process of generating linear image data 20 may be performed at any timing as long as the process of determining the arrival time (step S110) has been executed.

In the process procedure described above, the process of displaying linear image data 20 (step S117) is executed after a reliability display request has been accepted (Yes at step 3115). However, the embodiments are not limited to this process procedure. For example, linear image data 20 may be automatically displayed without a reliability display request having been accepted. That is, the processing at step S115 may not be executed.

As described above, the ultrasonic diagnosis apparatus 10 according to the first embodiment generates linear image data representing a line on which the arrival times, i.e., when the shear wave reaches individual points in the scan area, are substantially the same as each other. The ultrasonic diagnosis apparatus 10 then superimposes the linear image data on ultrasonic image data.

For example, the ultrasonic diagnosis apparatus 10 generates linear image data 20 by extracting a plurality of points having a predetermined arrival time from the points in the ROI and connecting the extracted points. In this manner, the ultrasonic diagnosis apparatus 10 can display linear image data 20 serving as scale marks of the arrival time on the arrival time image data as if contour lines are drawn on a map.

Here, linear image data 20 is displayed using the arrival time because the arrival time serves as an index of reliability of the stiffness of living tissue. For example, under an environment in which the stiffness of living tissue can be accurately measured due to the absence of displacement by the subject's body movement or reflection and refraction of the shear wave, the shear wave should propagate generally uniformly from the transmission position of a push pulse. As a result, the linear image data 20 of the arrival time is generally parallel to the transmission direction of the push pulse and forms a curved line in accordance with the stiffness of living tissue. By contrast, under an environment in which the stiffness of living tissue cannot be accurately measured, the propagation of the shear wave is observed extremely early or observed extremely late. As a result, the linear image data 20 of the arrival time becomes widely curved.

The operator thus can judge the reliability of stiffness of living tissue in an area in the vicinity of linear image data 20 by viewing the degree of the curve of linear image data 20 superimposed on ultrasonic image data.

In addition, for example, the ultrasonic diagnosis apparatus 10 assigns a pixel value corresponding to the arrival time to each linear image data 20. The operator thus can know the value of the arrival time in the neighborhood of each linear image data 20 by viewing the pixel value (color) of that linear image data 20.

Second Embodiment

In the first embodiment described above, the pixel value corresponding to the arrival time is assigned to linear image data 20. However, the embodiments are not limited thereto. For example, the ultrasonic diagnosis apparatus 10 may assign a pixel value corresponding to another parameter to linear image data 20. In a second embodiment described below, the ultrasonic diagnosis apparatus 10 assigns a pixel value corresponding to another parameter to linear image data 20.

Figure 7:
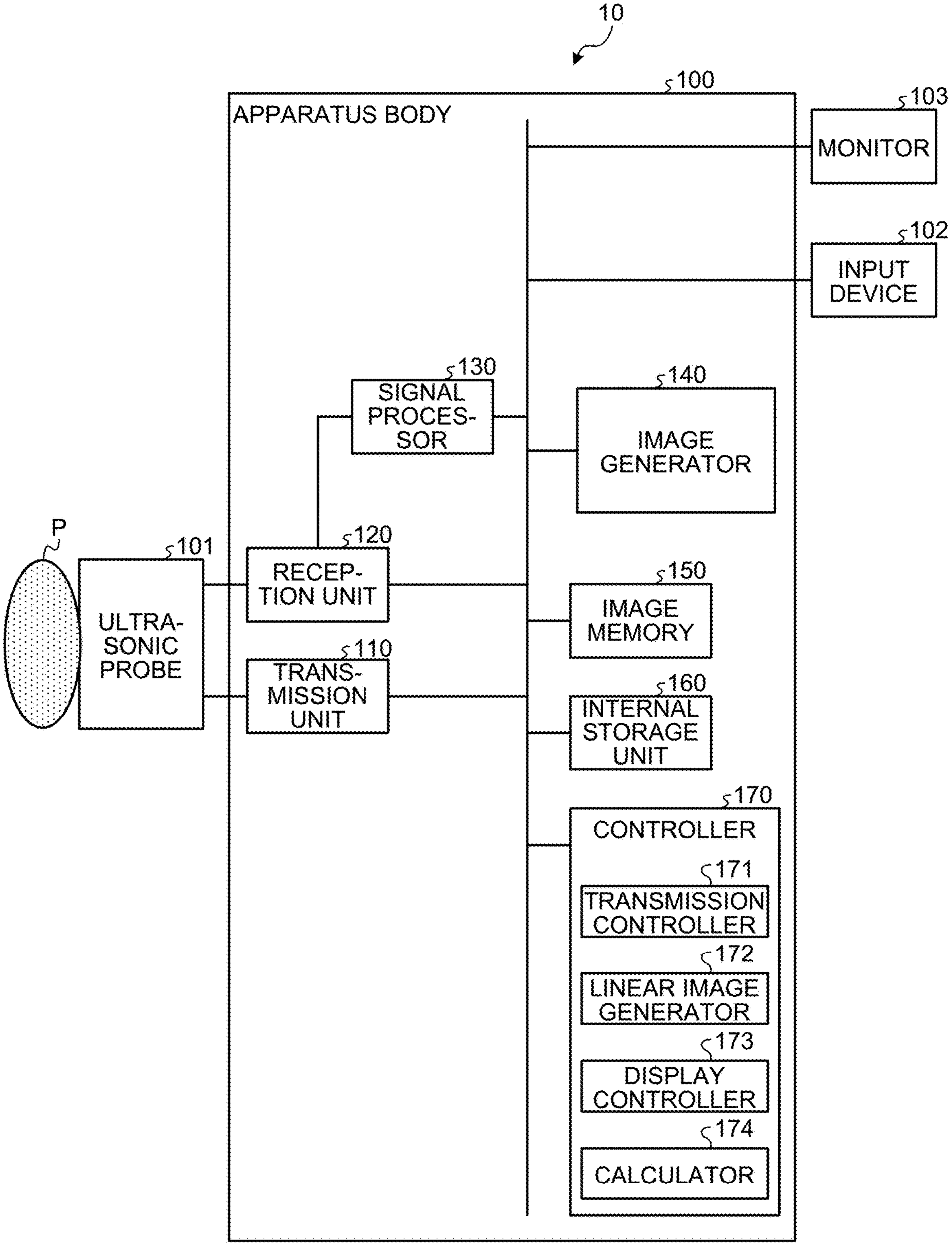
FIG. 7 is a block diagram illustrating a configuration example of the ultrasonic diagnosis apparatus according to a second embodiment.

FIG. 7 is a block diagram illustrating a configuration example of the ultrasonic diagnosis apparatus 10 according to the second embodiment. The ultrasonic diagnosis apparatus 10 according to the second embodiment, while having the same configuration as the ultrasonic diagnosis apparatus 10 illustrated in FIG. 1, differs in that it further includes a calculator 174 and in part of the process to be performed by the linear image generator 172. In the second embodiment, the differences from the first embodiment are mainly described, and the same functions as those in the configuration described in the first embodiment are denoted with the same reference signs as in FIG. 1 and a description thereof is omitted.

The calculator 174 according to the second embodiment calculates, for each point included in linear image data 20, a variance of the arrival times at individual points in a predetermined area including the foregoing point.

Figure 8:
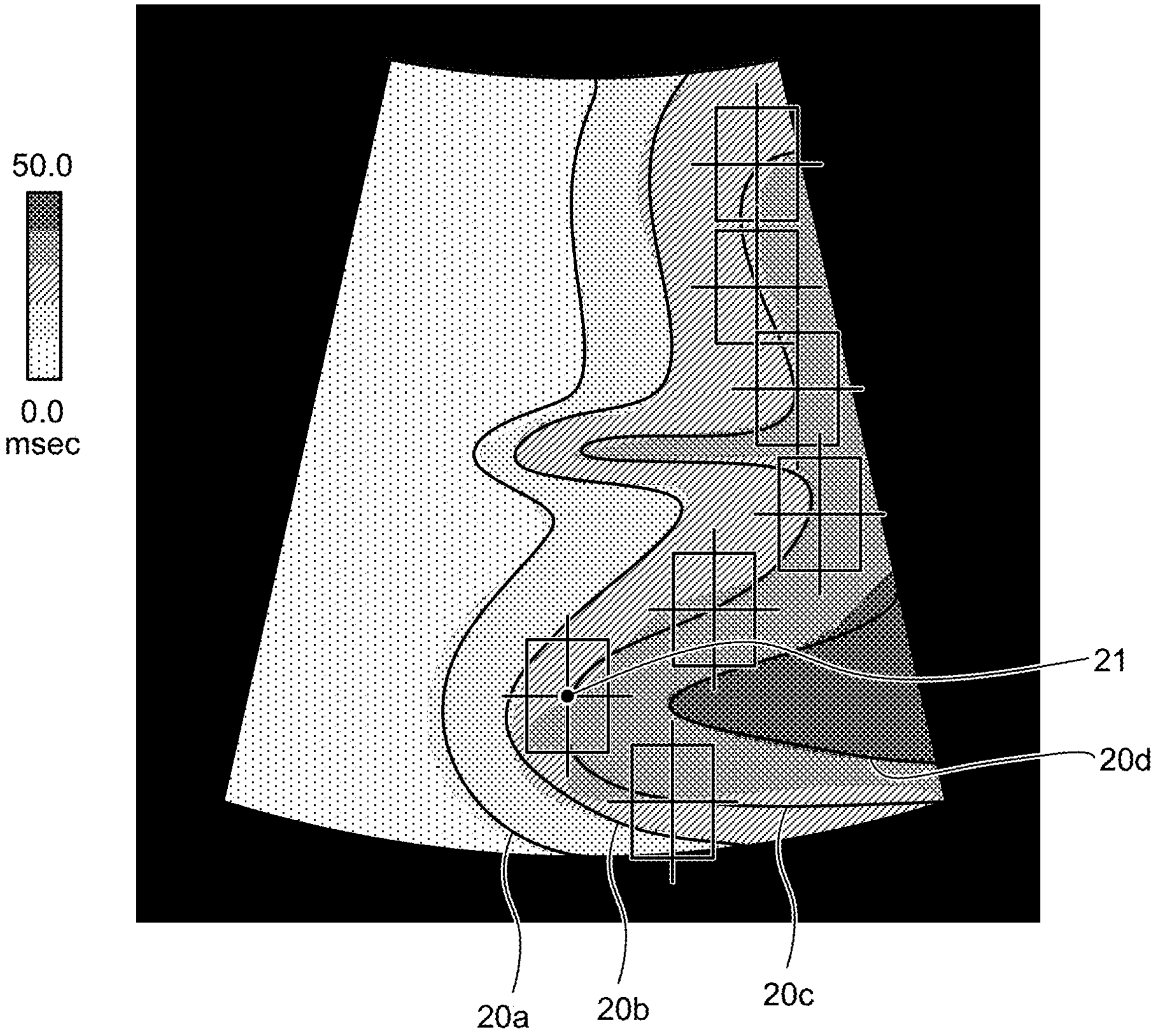
FIG. 8 is a diagram for explaining a process to be performed by a calculator according to the second embodiment.
Figure 9:
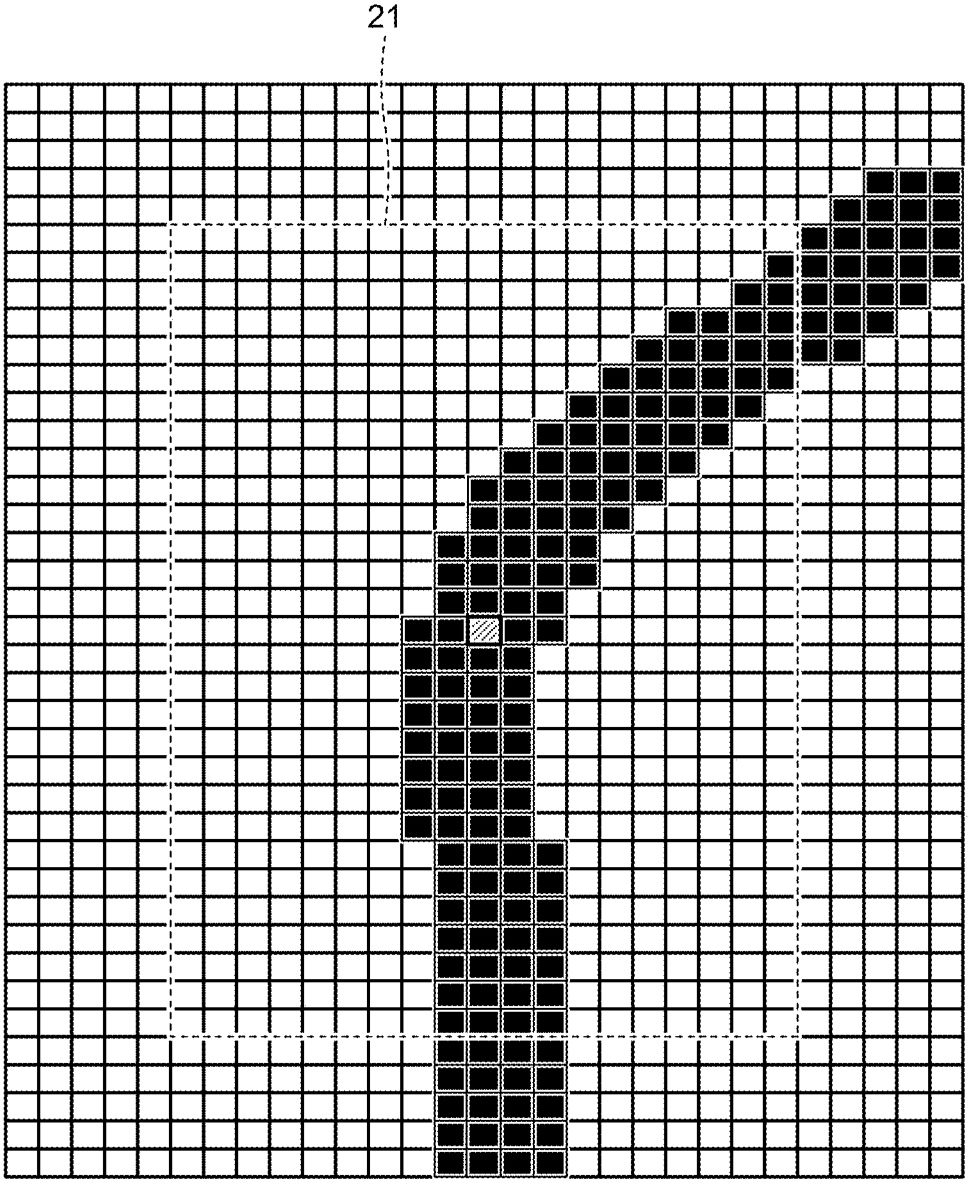
FIG. 9 is a diagram for explaining the process to be performed by the calculator according to the second embodiment.

FIG. 8 and FIG. 9 are diagrams for explaining a process to be performed by the calculator 174 according to the second embodiment. FIG. 8 illustrates a case where a variance calculation area 21 is arranged on arrival time image data and linear image data 20 similar to those in FIG. 3. Here, the variance calculation area 21 is an area having a predetermined size, with each point included in linear image data 20 at the center, for calculating a variance. Although this size is preset, the preset value may be changed as desired. FIG. 9 illustrates an enlarged view of the neighborhood of the variance calculation area 21 in FIG. 8. In FIG. 9, each black rectangle represents a point (pixel) included in the linear image data 20*c*. The shaded rectangle represents the center point (center pixel) of the variance calculation area 21.

As illustrated in FIG. 8, the calculator 174 arranges the variance calculation area 21, for example, with a point included in the linear image data 20*c* at the center. As illustrated in FIG. 9, the calculator 174 calculates the variance of the arrival times at individual points included in the arranged variance calculation area 21, as the variance at the center point. The calculator 174 then arranges the variance calculation area 21 for other points included in the linear image data 20*c* in the same manner, with each point at the center, and calculates the variance for each point included therein. The calculator 174 thus calculates the variance for each point included in the linear image data 20*c*.

For the linear image data 20*a*, 20*b*, 20*d*, the calculator 174 also calculates the variance for each point included in each of the linear image data 20*a*, 20*b*, 20*d* in the same manner. Each point of linear image data 20 thus has the variance of the arrival times as a parameter corresponding to the variation in arrival times at the surrounding points.

FIG. 8 and FIG. 9 merely illustrate an example. For example, although the description here provides the example in which the variance for each point is calculated on the arrival time image data (FIG. 3) for convenience of explanation, the embodiments are not limited thereto. That is, the calculator 174 can calculate the variance for each point included in linear image data 20 even without performing the process on the arrival time image data.

The linear image generator 172 according to the second embodiment has the same functions as those described in the first embodiment and further assigns, to each point included in linear image data 20, a pixel value corresponding to the variance at the point. For example, the linear image generator 172 assigns, to each point included in linear image data 20, the pixel value corresponding to the variance of that point as calculated by the calculator 174.

Figure 10:
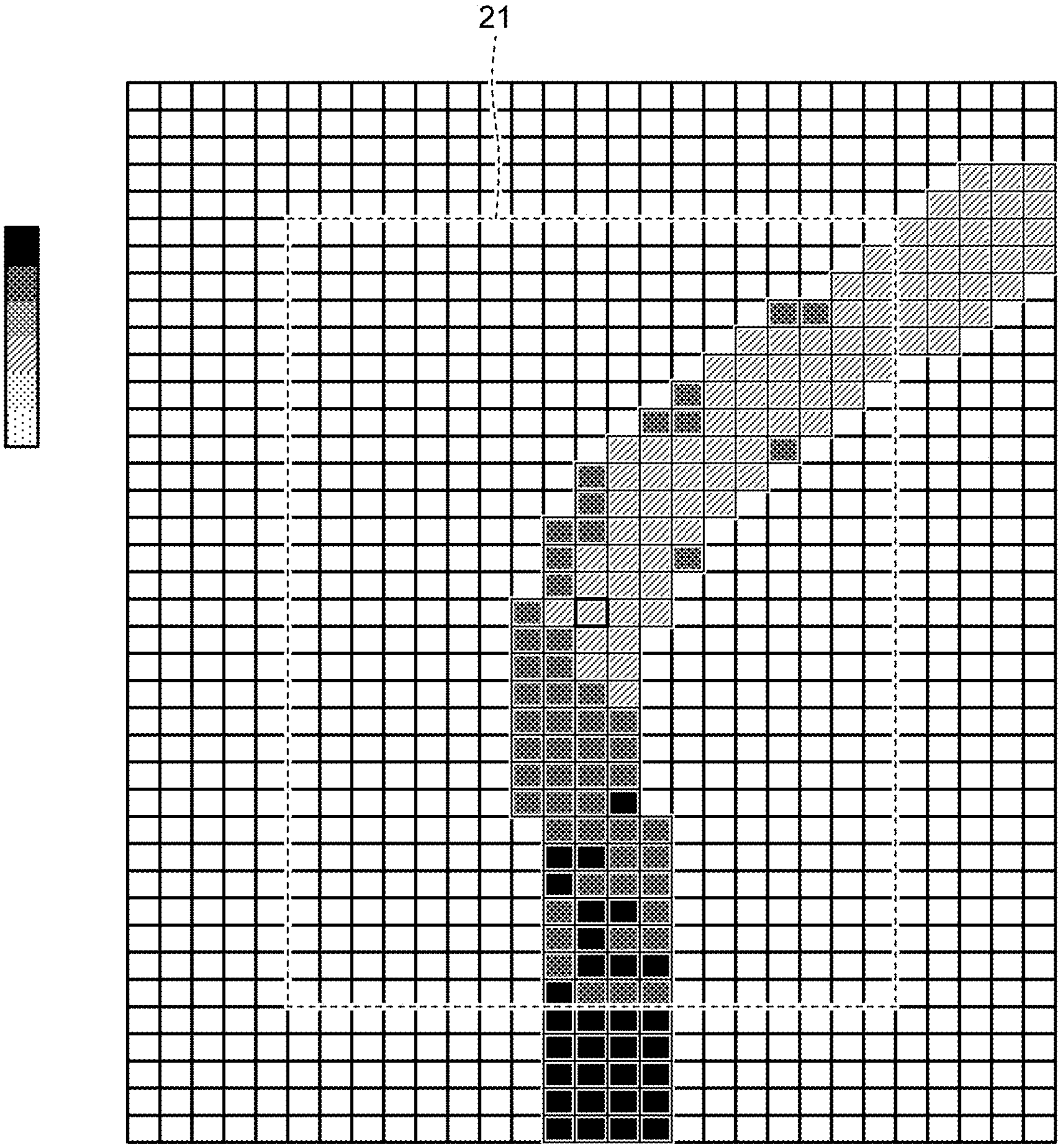
FIG. 10 is a diagram for explaining a process to be performed by the linear image generator according to the second embodiment.

FIG. 10 is a diagram for explaining a process to be performed by the linear image generator 172 according to the second embodiment. FIG. 10 illustrates an example in which the pixel value corresponding to the variance at each point included in the linear image data 20*c* in FIG. 9 is assigned to that point.

As illustrated in FIG. 10, the linear image generator 172 assigns, to each point included in the linear image data 20*c* in FIG. 9, the pixel value corresponding to the variance at that point as calculated by the calculator 174. As an example, the linear image generator 172 assigns blue, blue green, yellow green, yellow, orange, and red in the increasing order of the variance for each point.

It is noted that FIG. 10 merely illustrates an example. For example, in the example in FIG. 10, the pixel value corresponding to the variance at each point included in linear image data 20 is assigned to that point. However, the embodiments are not limited to this example. For example, the linear image generator 172 may assign a hatching pattern different by variance at each point, to each point included in linear image data 20.

For the linear image data 20*a*, 20*b*, 20*d*, the linear image generator 172 also assigns the pixel value corresponding to the variance at each point included in each of the linear image data 20*a*, 20*b*, 20*d*, in the same manner. Each point of linear image data 20 appearing on the monitor 103 thus has the color corresponding to a variation in arrival times at the surrounding points.

As described above, the ultrasonic diagnosis apparatus 10 according to the second embodiment calculates, for each point included in linear image data 20, the variance of the arrival times at the respective points in a predetermined area including the foregoing point. The ultrasonic diagnosis apparatus 10 then assigns, to each point included in linear image data 20, the pixel value corresponding to the variance at that point.

Here, the pixel value (color) is assigned (color-coded) to each point included in linear image data 20 using the variance, because the variance serves an index of reliability of the stiffness of living tissue. For example, in the second embodiment, each point of linear image data 20 appearing on the monitor 103 has the color corresponding to the variation in arrival times at the surrounding points. Here, under an environment in which the stiffness of living tissue can be accurately measured, the variance is not high since the shear wave propagates generally uniformly. By contrast, if the propagation of the shear wave is disrupted in living tissue, the variance is high. It can be judged that the reliability of stiffness is low in the area having high variances.

The operator thus can judge the reliability of the stiffness of living tissue in the area in the vicinity of linear image data 20 by viewing the pixel value (color) assigned to each point included in the linear image data 20.

In the second embodiment described above, to each point in linear image data 20, the pixel value corresponding to the variance at the point is assigned. However, the embodiments are not limited thereto. For example, the ultrasonic diagnosis apparatus 10 may assign, to each point in linear image data 20, the pixel value corresponding to a parameter such as the index value (shear wave speed, Young's modulus, or shear modulus) of the stiffness of living tissue at each point or the magnitude of displacement at each point. The operator thus can easily recognize information suggested by a variety of parameters by viewing the color of each point of linear image data 20.

Third Embodiment

The first and the second embodiments described above illustrated a case in which linear image data 20 is displayed using the arrival time. However, the embodiments are not limited thereto. For example, the ultrasonic diagnosis apparatus 10 may display an image serving as such a scale mark as linear image data 20 using another parameter. In a third embodiment, the ultrasonic diagnosis apparatus 10 displays an image serving as such a scale mark as linear image data 20 using another parameter.

The ultrasonic diagnosis apparatus 10 according to the third embodiment has the same configuration as the ultrasonic diagnosis apparatus 10 illustrated FIG. 1 and differs in part of the process to be performed by the linear image generator 172 and the display controller 173. In the third embodiment, the differences from the first embodiment are mainly described, and the same functions as those in the configuration illustrated in the first embodiment are denoted with the same reference signs as in FIG. 1 and a description thereof is omitted.

The linear image generator 172 according to the third embodiment has the same functions as those described in the first embodiment and further generates stiffness linear image data representing a line on which the index values of the stiffness of living tissue based on the shear wave at individual points in the scan area are substantially the same as each other. For example, the linear image generator 172 extracts a plurality of points having an index value with a predetermined magnitude from the points in the scan area. The linear image generator 172 then generates stiffness linear image data by connecting the extracted points. The index value with a predetermined magnitude is a value designated beforehand by the operator or the designer of the ultrasonic diagnosis apparatus 10, and a plurality of values are usually designated.

Figure 11:
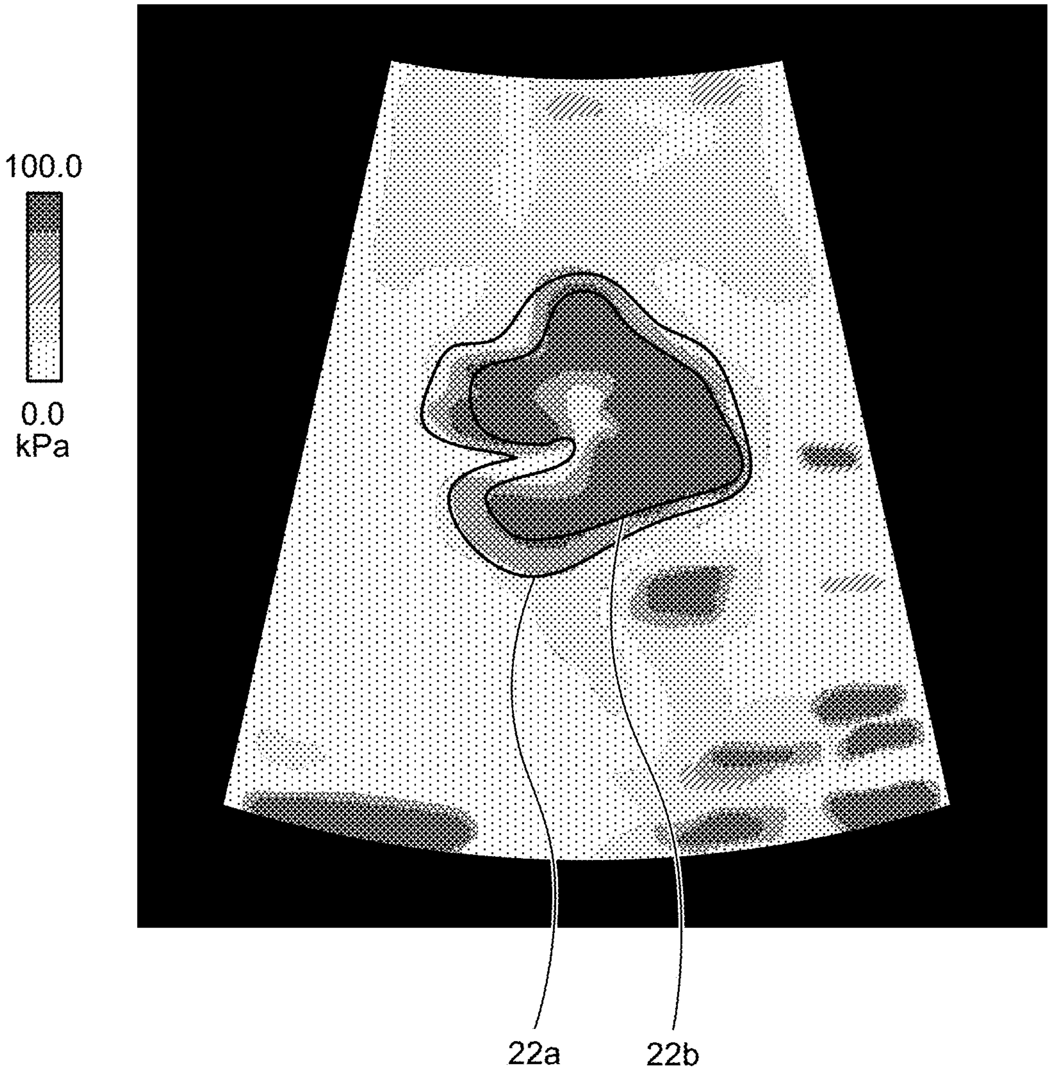
FIG. 11 is a diagram for explaining the process to be performed by the linear image generator according to a third embodiment.

FIG. 11 is a diagram for explaining the process to be performed by the linear image generator 172 according to the third embodiment. FIG. 11 illustrates a case where linear image data 22*a* and 22*b* generated by the linear image generator 172 are displayed on the stiffness image data in FIG. 2. The linear image data 22*a* represents positions where the Young's modulus is 30 [kPa], and the linear image data 22*b* represents positions where the Young's modulus is 60 [kPa]. The linear image data 22*a* and 22*b* are collectively denoted as "linear image data 22" unless it is necessary to distinguish them from each other. This linear image data 22 is an example of the stiffness position image data.

As illustrated in FIG. 11, the linear image generator 172 acquires the stiffness image data generated by the image generator 140. The linear image generator 172 then extracts a plurality of points where the Young's modulus is 30 [kPa] from the acquired stiffness image data. The linear image generator 172 then generates linear image data 22*a* by connecting the extracted points. The linear image generator 172 also generates linear image data 22*b* by connecting the points corresponding to 60 [kPa] in the same manner as in the linear image data 22*a*.

The linear image generator 172 assigns, for example, to each piece of the linear image data 22, a pixel value corresponding to the index value of stiffness (here, the Young's modulus) thereof. In the example illustrated in FIG. 11, the linear image generator 172 assigns, to each piece of the linear image data 22*a* and 22*b*, the pixel value corresponding to the Young's modulus. Specifically, the linear image generator 172 assigns yellow green to the linear image data 22*a* and assigns orange to the linear image data 22*b*.

As described above, the linear image generator 172 generates linear image data 22*a* and 22*b* representing the positions where the Young's moduli are 30 and 60 [kPa], respectively.

It is noted that FIG. 11 merely illustrates an example. For example, in the example in FIG. 11 described above, linear image data 22 are generated at the positions where the Young's moduli are 30 and 60 [kPa]. However, the embodiments are not limited thereto. For example, the linear image generator 172 may generate linear image data 22 at positions corresponding to any desired Young's modulus or may generate any desired number of pieces of linear image data 22.

In the example in FIG. 11 described above, a pixel value corresponding to the Young's modulus is assigned to each piece of linear image data 22. However, the embodiments are not limited to this example. For example, the linear image generator 172 may assign different kinds of lines (solid line, dashed line, dotted line, dashed and single-dotted line, and other lines) to pieces of linear image data 22 with different Young's modulus values.

In the description here, linear image data 22 is generated after stiffness image data (FIG. 2) is generated, for convenience of explanation. However, the embodiments are not limited thereto. That is, the linear image generator 172 can generate stiffness linear image data 22 even when stiffness image data is not generated. For example, the linear image generator 172 may generate linear image data 22 by extracting a plurality of points having a predetermined Young's modulus among the Young's moduli at individual points as determined by the signal processor 130.

Although not described here, the linear image generator 172 may perform, for example, smoothing processing for smoothing linear image data 22 or may perform processing for making the thickness of linear image data 22 uniform, when generating linear image data 22. When extracting the points having a predetermined Young's modulus, the linear image generator 172 may perform the extraction, for example, allowing a margin of error to such an extent that the extracted points form a linear shape, rather than extracting only the points that exactly match the predetermined Young's modulus. That is, the "line on which the index values of stiffness are substantially the same as each other" refers to a line that is based on a plurality of points having the same index value of stiffness within a margin of error to such an extent that the extracted points form a linear shape and that has been subjected to the smoothing processing or the processing for making the thickness uniform.

The display controller 173 according to the third embodiment has the same functions as those described in the first embodiment and further superimposes linear image data 22 on ultrasonic image data. For example, the display controller 173 superimposes the linear image data 22 generated by the linear image generator 172 on the arrival time image data.

Figure 12:
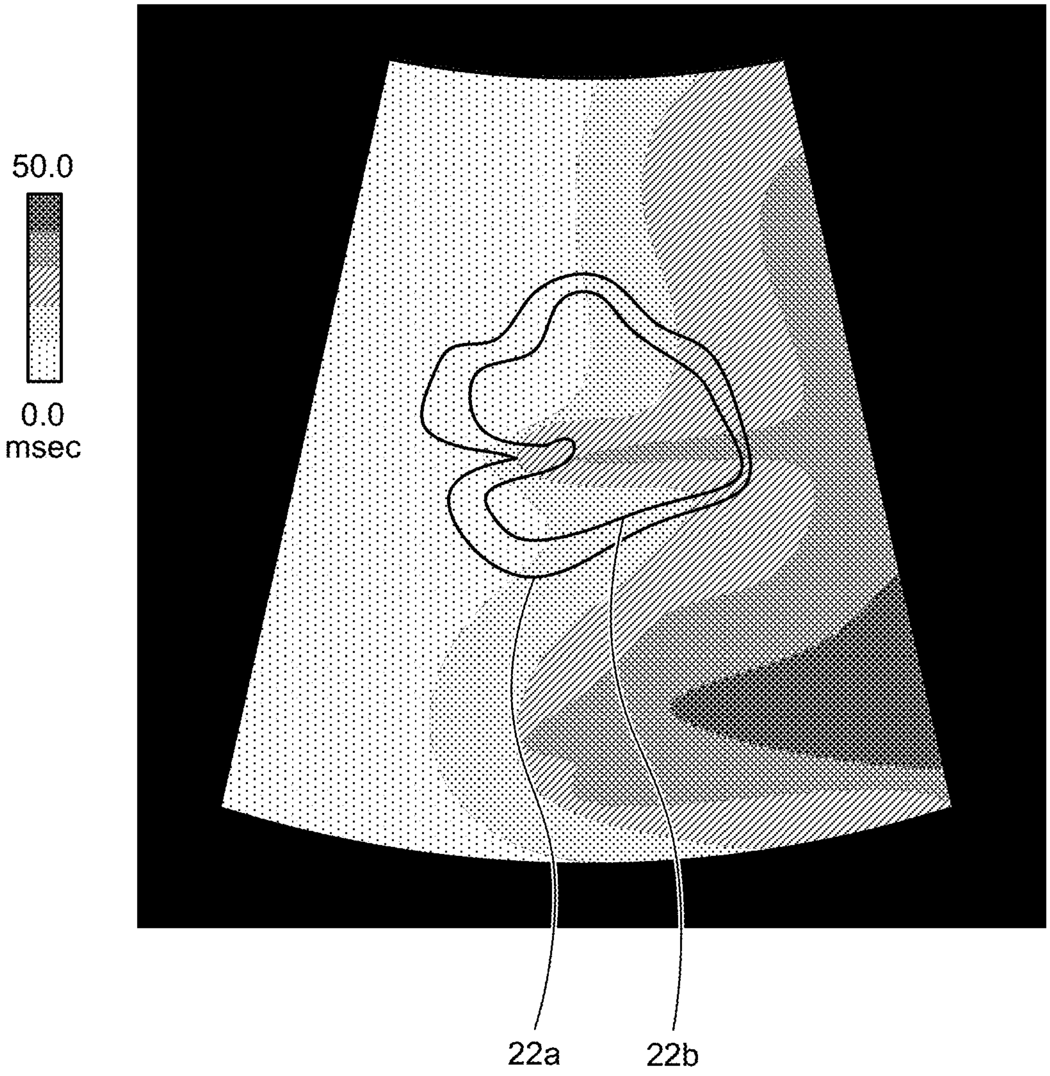
FIG. 12 is a diagram illustrating an example of a display image displayed by the display controller according to the third embodiment.

FIG. 12 is a diagram illustrating an example of a display image displayed by the display controller 173 according to the third embodiment. As illustrated in FIG. 12, the display controller 173 displays linear image data 22*a* and 22*b* generated in FIG. 11 on the arrival time image data illustrated in FIG. 3.

It is noted that FIG. 12 merely illustrates an example. For example, in FIG. 12, linear image data 22 is superimposed on the arrival time image data used as a background image. However, the background image is not limited to this image data. For example, B mode image data, the stiffness image data in FIG. 2, displacement image data described later, or variance image data described later may be used as a background image.

As described above, the ultrasonic diagnosis apparatus 10 according to the third embodiment generates linear image data 22 using an index value of stiffness. The ultrasonic diagnosis apparatus 10 then superimposes the generated linear image data 22 on ultrasonic image data. The operator thus can visually grasp, for example, the relevance between the index value of stiffness and the parameter in the background image.

In the third embodiment described above, the index value of stiffness is used as a parameter other than the arrival time to generate scale marks (contour lines). However, the embodiments are not limited thereto. For example, the linear image generator 172 may generate a scale mark using the magnitude of displacement at each point. Specifically, the linear image generator 172 may generate image data (displacement position image data) representing a line on which the magnitudes of displacement at individual points in the scan area are substantially the same as each other. The display controller 173 then displays the generated displacement position image data on ultrasonic image data. The ultrasonic diagnosis apparatus 10 thus displays such a scale mark as linear image data 20 using the parameter different from that in the background image, so that the operator can visually grasp the relevance between those different parameters.

The ultrasonic diagnosis apparatus 10 according to the third embodiment may select image data of any desired kinds from the linear image data 20 based on the arrival times, the linear image data 22, and the displacement position image data and superimpose all of image data of the selected kinds on ultrasonic image data. That is, the ultrasonic diagnosis apparatus 10 may superimpose, for example, the linear image data 20 based on the arrival times and the linear image data 22 on ultrasonic image data of one kind.

The process in which the ultrasonic diagnosis apparatus 10 according to the third embodiment uses another parameter to display an image serving such a scale mark as linear image data 20 may be executed independently of the process of generating and displaying the linear image data 20 based on the arrival times.

Fourth Embodiment

For example, the ultrasonic diagnosis apparatus 10 may display an image serving as such a scale mark as linear image data 20 based on the arrival times in a case where the shear wave propagates throughout the entire scan area with a shear wave speed in a predetermined area. In a fourth embodiment described below, the ultrasonic diagnosis apparatus 10 displays an image serving as such a scale mark as linear image data 20 based on the arrival times in a case where the shear wave propagates throughout the entire scan area with a shear wave speed in a predetermined area.

The ultrasonic diagnosis apparatus 10 according to the fourth embodiment has the same configuration as the ultrasonic diagnosis apparatus 10 illustrated in FIG. 1 and differs in part of the process to be performed by the linear image generator 172 and the display controller 173. In the fourth embodiment, the differences from the first embodiment are mainly described, and the same functions as those in the configuration described in the first embodiment are denoted with the same reference signs as in FIG. 1 and a description thereof is omitted.

The linear image generator 172 according to the fourth embodiment has the same functions as those described in the first embodiment. The linear image generator 172 further calculates the arrival time when the shear wave reaches each point in the scan area with the propagation speed of the shear wave in a predetermined area and generates predetermined area position image data representing a line on which the calculated arrival times are substantially the same as each other.

Figure 13:
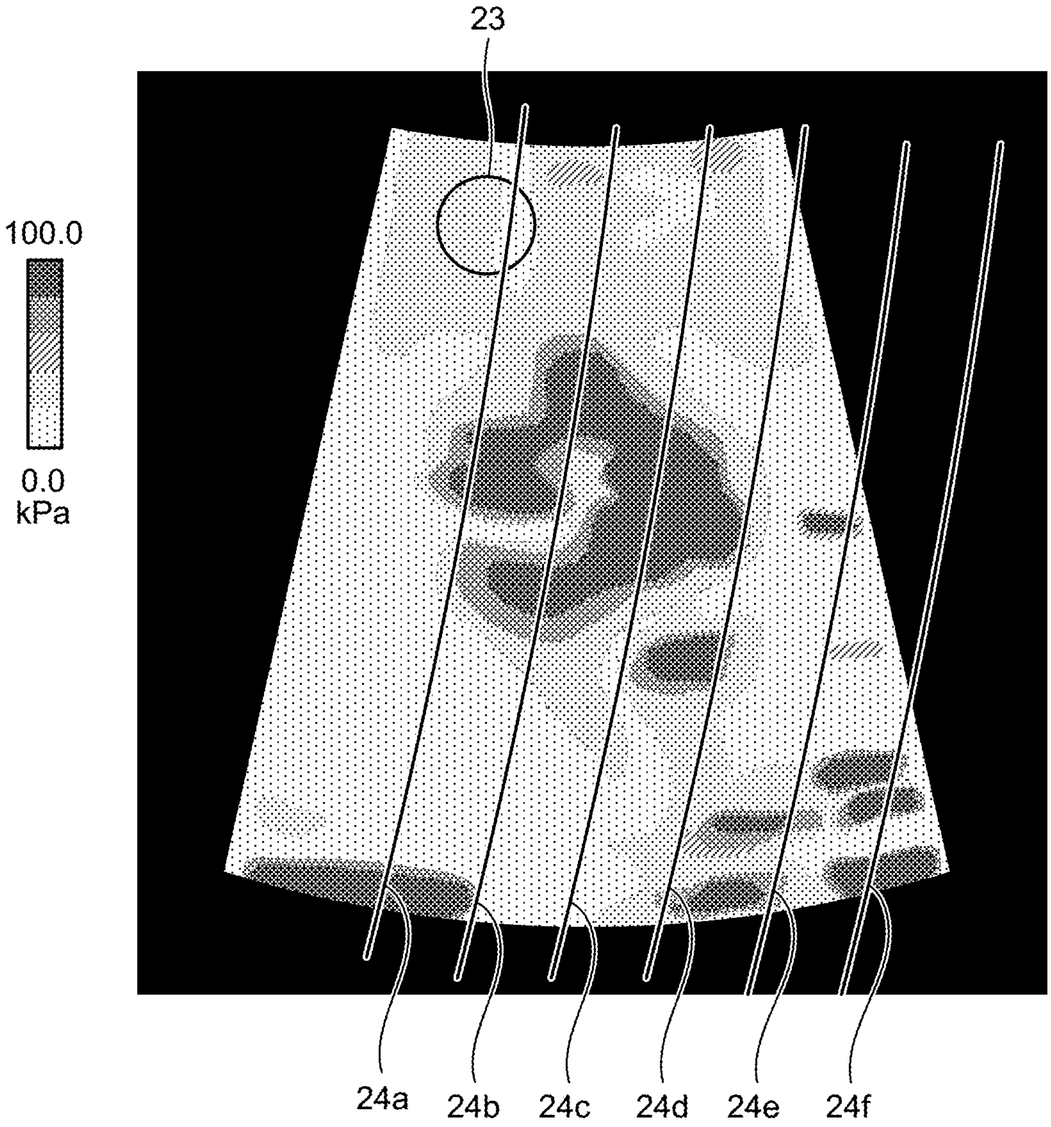
FIG. 13 is a diagram for explaining a process to be performed by the linear image generator according to a fourth embodiment.

FIG. 13 is a diagram for explaining a process to be performed by the linear image generator 172 according to the fourth embodiment. FIG. 13 illustrates a case where an ROI 23 designated by the operator and linear image data 24*a* to 24*f* are displayed on the stiffness image data in FIG. 2. In FIG. 13, the linear image data 24*a* represents positions where the arrival time is 5 [msec], the linear image data 24*b* represents positions where the arrival time is 10 [msec], the linear image data 24*c* represents positions where the arrival time is 15 [msec], the linear image data 24*d* represents positions where the arrival time is 20 [msec], the linear image data 24*e* represents positions where the arrival time is 25 [msec], and the linear image data 24*f* represents positions where the arrival time is 30 [msec]. The linear image data 24*a* to 24*f* are collectively referred to as "linear image data 24" unless it is necessary to distinguish them from each other. This linear image data 24 is an example of the predetermined area position image data.

As illustrated in FIG. 13, the linear image generator 172 accepts, for example, an operation to designate the ROI 23 from the operator. The linear image generator 172 then calculates a mean value of the shear wave speeds at individual points included in the accepted ROI 23. The linear image generator 172 then calculates the arrival time when the shear wave reaches each point in the scan area with the calculated mean value of the shear wave speeds. In other words, the linear image generator 172 calculates the arrival time at each point in the scan area, assuming that all the points in the scan area have uniform stiffness (average stiffness in the ROI 23) and the shear wave propagates throughout the entire scan area with a constant speed (the calculated mean value of the shear wave speeds). For example, the linear image generator 172 calculates the arrival time at each point using the calculated mean value of the shear wave speeds and the distance from the transmission position of a push pulse to each point. The linear image generator 172 then generates linear image data 24*a* to 24*f* each representing a line on which the calculated arrival times are substantially the same as each other. Here, the linear image data 24*a* to 24*f* are parallel lines to the transmission position of a push pulse because they are generated assuming that all the points in the scan area have average stiffness in the ROI 23. In FIG. 13, it is assumed that the transmission position of a push pulse is at the left end of the scan area. The process in which the linear image generator 172 generates linear image data 24*a* to 24*f* each representing positions where the calculated arrival times are substantially the same as each other is the same as described in the first embodiment and a detailed description thereof is omitted.

It is noted that FIG. 13 merely illustrates an example. For example, the linear image generator 172 may generate linear image data 24 at positions corresponding to any desired arrival time or may generate any desired number of individual lines of linear image data 24.

For example, the linear image generator 172 may assign a pixel value corresponding to the calculated arrival time to each piece of linear image data 24. For example, the linear image generator 172 may assign different kinds of lines (solid line, dashed line, dotted line, dashed and single-dotted line, and other lines) to lines of linear image data 24 that correspond to different calculated arrival times.

For example, if the position and size of the ROI 23 are preset, the designation of the ROI 23 by the operator may not necessarily be required. For example, if the ROI 23 preset is used as it is, the designation of the ROI 23 by the operator may not be accepted.

In FIG. 13 described above, the stiffness image data is used as a background image. However, the embodiments are not limited thereto. For example, the linear image generator 172 may execute the processing described above, irrespective of the presence or absence of a background image and the kind of ultrasonic image data serving as a background image.

In FIG. 13 described above, the mean value of the shear wave speeds at individual points included in the ROI 23 is used. However, the embodiments are not limited thereto. For example, the shear wave speed at the center point of the ROI 23 may be used.

The display controller 173 according to the fourth embodiment has the same functions as those described in the first embodiment and further displays linear image data 24 on ultrasonic image data.

For example, the display controller 173 superimposes the linear image data 24 generated by the linear image generator 172 on the arrival time image data.

Figure 14:
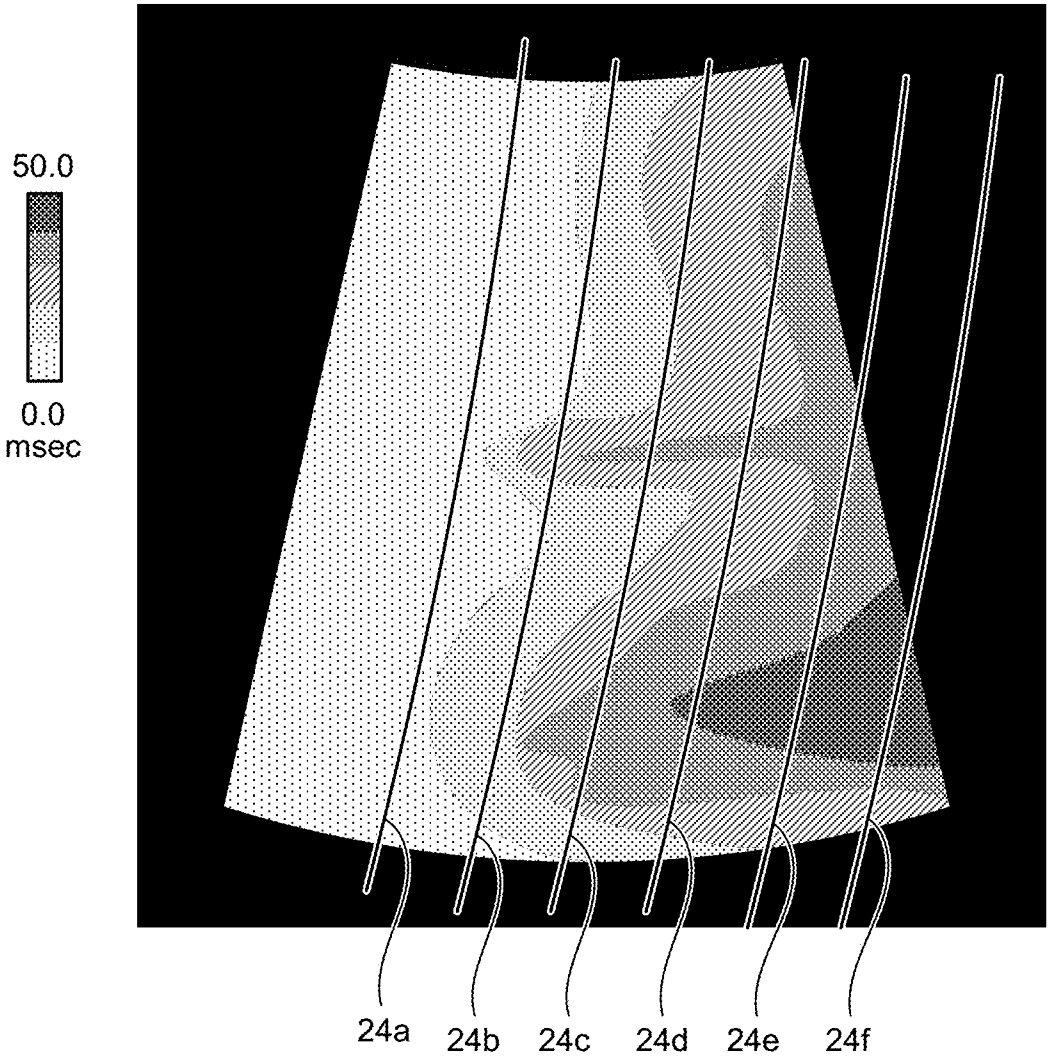
FIG. 14 is a diagram illustrating an example of a display image displayed by the display controller according to the fourth embodiment.

FIG. 14 is a diagram illustrating an example of a display image displayed by the display controller 173 according to the fourth embodiment. As illustrated in FIG. 14, the display controller 173 displays the linear image data 24 generated in FIG. 13 on the arrival time image data illustrated in FIG. 3.

It is noted that FIG. 14 merely illustrates an example. For example, in FIG. 14 described above, the linear image data 24 is superimposed on the arrival time image data used as a background image. However, the background image is not limited to this image data. For example, B mode image data, the stiffness image data in FIG. 2, displacement image data described later, or variance image data described later may be used as a background image.

As described above, the ultrasonic diagnosis apparatus 10 according to the fourth embodiment displays an image serving as such a scale mark as linear image data 20 based on the arrival times in a case where the shear wave propagates throughout the entire scan area with the shear wave speed in the ROI 23. The operator thus can easily compare the arrival time in a case where the shear wave propagates throughout the entire scan area with the shear wave speed in the ROI 23, with another parameter.

The ultrasonic diagnosis apparatus 10 according to the fourth embodiment may superimpose the linear image data 24 displayed here, together with image data of any desired kind or kinds out of the linear image data 20 based on the arrival times, the linear image data 22, and the displacement position image data, on ultrasonic image data. The operator thereby can compare a plurality of parameters on the same ultrasonic image data.

The process to be performed by the ultrasonic diagnosis apparatus 10 according to the fourth embodiment to display an image serving as such a scale mark as linear image data 20 based on the arrival times in a case where the shear wave propagates throughout the entire scan area with the shear wave speed in a predetermined area may be executed independently of the process of generating and displaying the linear image data 20 based on the arrival times.

Other Embodiments

The first to the fourth embodiments have been described so far. Other than those embodiments, a variety of modifications thereof may be carried out. It is noted that each process described below can be executed independently of the process of generating and displaying the linear image data 20 of the arrival time.

Generation of Displacement Image Data

For example, the ultrasonic diagnosis apparatus 10 may generate displacement image data in which the pixel value corresponding to the magnitude of displacement at each point is assigned to each point in the scan area.

For example, the image generator 140 generates displacement image data by assigning the pixel value corresponding to the magnitude of displacement at each point to each point in the scan area. Specifically, the image generator 140 acquires displacement at each point in the scan area that is calculated by the signal processor 130 over a plurality of time phases. The image generator 140 then specifies the amount of displacement (maximum amount of displacement) that is the greatest among the displacements calculated over a plurality of time phases, for each point. The image generator 140 then generates displacement image data by assigning the pixel value corresponding to the specified maximum amount of displacement at each point to each point.

Figure 15:
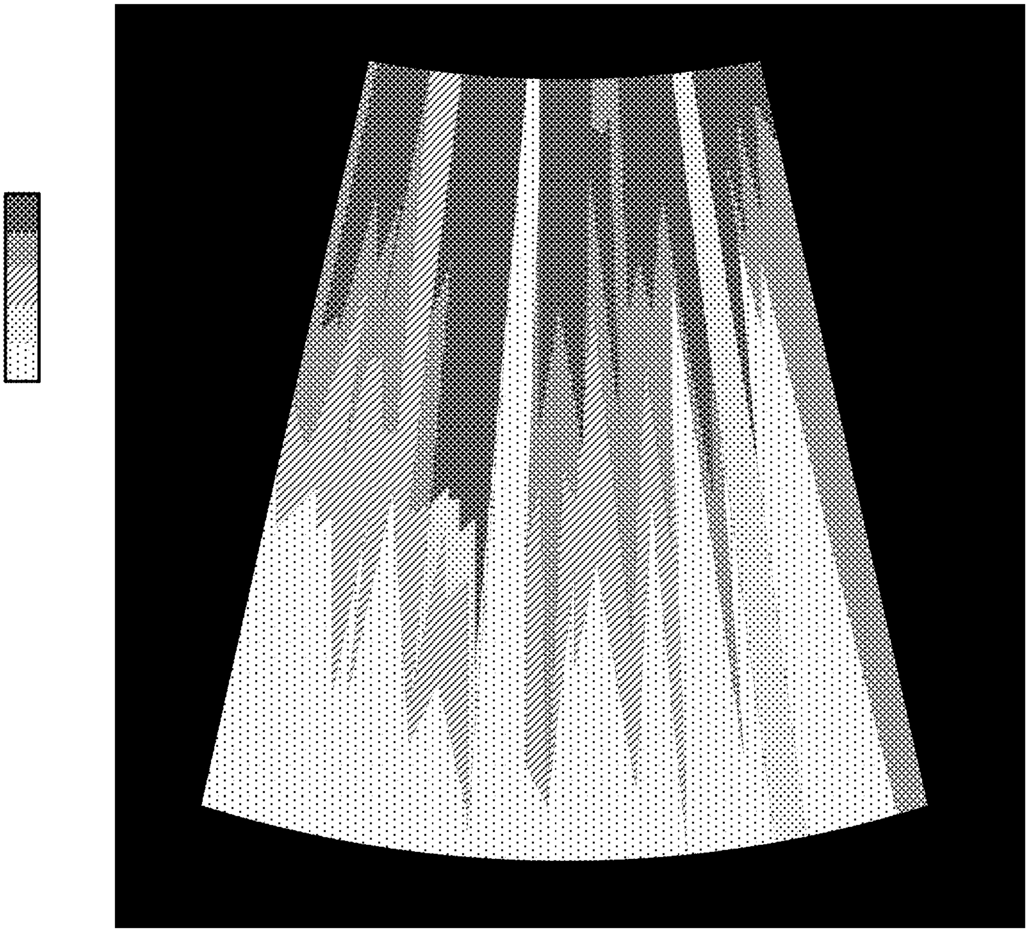
FIG. 15 is a diagram for explaining displacement image data.

FIG. 15 is a diagram for explaining displacement image data. As illustrated in FIG. 15, the image generator 140 generates displacement image data in which the points in the scan area are color-coded based on the maximum amounts of displacement.

As described above, the image generator 140 generates displacement image data by assigning the pixel value corresponding to the magnitude of displacement at each point to each point in the scan area. Here, displacement image data is generated because the magnitude of displacement serves as an index of the reliability of the stiffness of living tissue. For example, if displacement large enough to be observed with the observation pulse occurs at each point in the scan area, the reliability of the stiffness of living tissue observed is high. By contrast, if displacement large enough does not occur at each point in the scan area, the observation with the observation pulse is difficult. The reliability of the stiffness of living tissue observed is therefore low. The operator thus can easily grasp the reliability of the stiffness of living tissue observed, by viewing the displacement image data.

In the example illustrated in FIG. 15, it is understood that the displacement is larger at a point in the upper position in the scan area, and the reliability is high. On the other hand, it is understood that the displacement is smaller at a point in the lower position in the scan area, and the reliability is low.

In the example in FIG. 15 described above, the maximum amount of displacement is used as the magnitude of displacement at each point. However, the embodiments are not limited to this example. For example, displacement image data may be generated by assigning the pixel value corresponding to the integral value (the sum of amounts of displacement in a certain time period) in a time-displacement curve to each point. Alternatively, displacement image data may be generated, for example, by assigning the pixel value corresponding to the differential value (the magnitude of the slope) in a time-displacement curve to each point. That is, displacement image data may be generated by assigning the pixel value corresponding to the time when the propagation speed of the shear wave is maximum, to each point.

Generation of Variance Image Data

For example, the ultrasonic diagnosis apparatus 10 may generate variance image data in which the pixel value corresponding to the variance at each point is assigned to the point in the scan area.

For example, the calculator 174 calculates, for each point in the scan area, the variance of the arrival times at individual points in a predetermined area including the foregoing point. As an example, the calculator 174 calculates the variance for each point in the scan area using the variance calculation area 21 in FIG. 8. The process of calculating the variance using the variance calculation area 21 is the same as described in the second embodiment and a detailed description thereof is omitted.

The image generator 140 then generates variance image data by assigning the pixel value corresponding to the variance at each point to each point in the scan area. Specifically, the image generator 140 acquires the variance at each point in the scan area as calculated by the calculator 174. The image generator 140 then generates variance image data by assigning the pixel value corresponding to the acquired variance to each point.

As described above, the image generator 140 generates variance image data by assigning the pixel value corresponding to the variance at each point to each point in the scan area. The operator thereby can easily grasp the reliability of the stiffness of living tissue observed, by viewing the variance image data.

Change of Image Data with Various Parameters

For example, the ultrasonic diagnosis apparatus 10 may change the pixel value at each point included in ultrasonic image data, using any one of parameters including the index value of stiffness, the arrival time of the shear wave, the magnitude of displacement, and the variance at each point.

The image generator 140 changes the pixel value at each point included in ultrasonic image data, using any one of parameters including the index value of stiffness, the arrival time of the shear wave, the magnitude of displacement, and the variance for each point.

Figure 16:
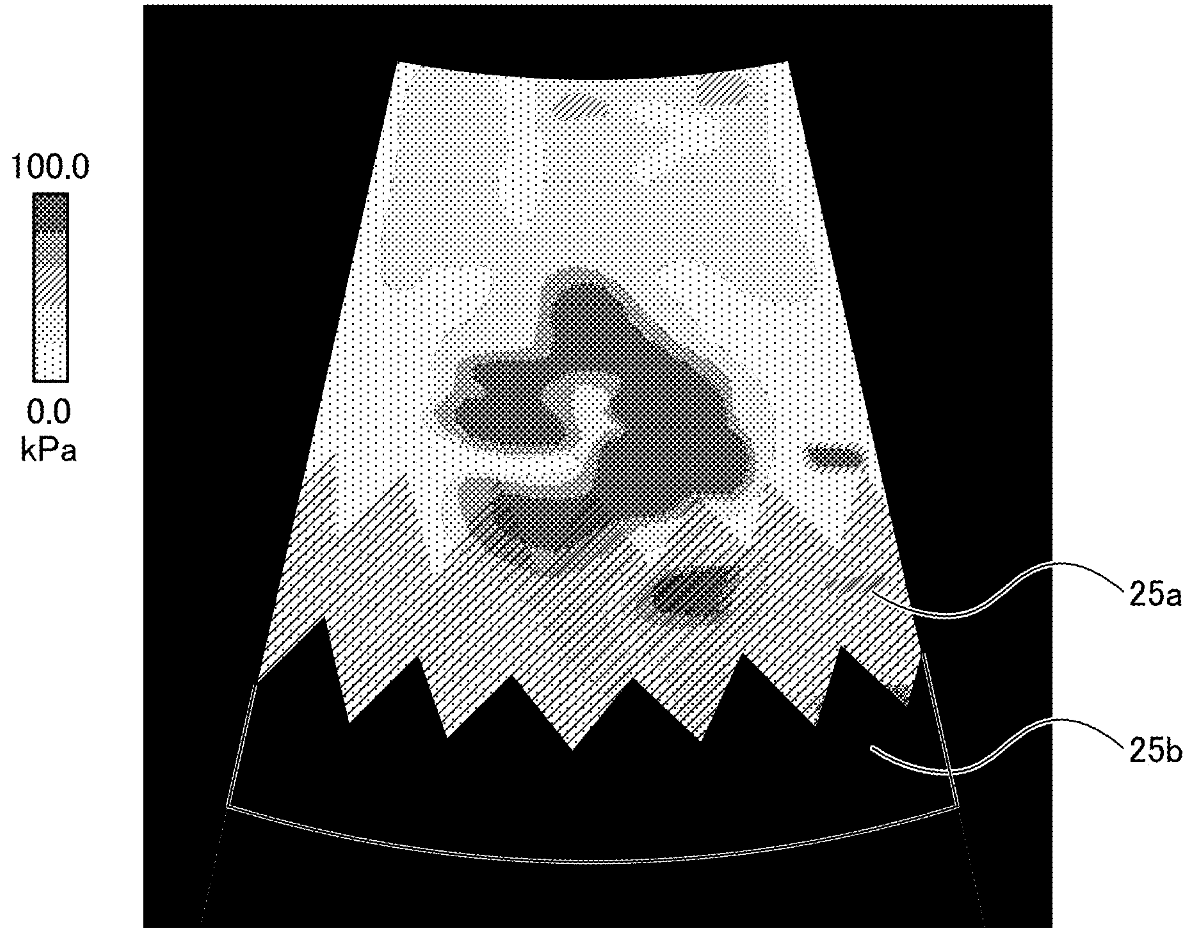
FIG. 16 is a diagram for explaining a process of changing brightness.

For example, the image generator 140 performs the process of changing the brightness of ultrasonic image data. FIG. 16 is a diagram for explaining the process of changing brightness. In FIG. 16, the process of changing the brightness of stiffness image data using the magnitude of displacement is described. In the example illustrated in FIG. 16, an area 25*a* in stiffness image data is dark and an area 25*b* is solid black. The upper area (the area above the area 25*a*) in the stiffness image data is displayed with the brightness of the original stiffness image data being kept.

For example, the image generator 140 evaluates the reliability on three levels, based on the magnitude of displacement at each point in the scan area. Specifically speaking, the image generator 140 determines that the reliability at the point at which the maximum amount of displacement is equal to or greater than a first threshold is "high". The image generator 140 determines that the point at which the maximum displacement is less than the first threshold and equal to or greater than a second threshold is "medium". Here, the second threshold is a value smaller than the first threshold. The image generator 140 determines that the reliability at the point at which the maximum displacement is less than the second threshold is "low". In the example illustrated in FIG. 16, the image generator 140 determines that the upper area in the stiffness image data is "high", the area 25*a* is "medium", and the area 25*b* is "low".

The image generator 140 keeps the brightness of the original image unchanged in the area determined to have "high" reliability. The image generator 140 darkens the original image in the area 25*a* determined to have "medium" reliability. For example, the image generator 140 darkens the image by subtracting a predetermined number from the RGB value at the points included in the area 25*a*. The image generator 140 fills the original image with solid black in the area 25*b* determined to have "low" reliability. For example, the image generator 140 fills the image with solid black by setting the RGB value at the points included in the area 25*b* to zero. As described above, the image generator 140 changes the brightness of the stiffness image data in FIG. 2 based on the magnitude of displacement at each point.

Figure 17:
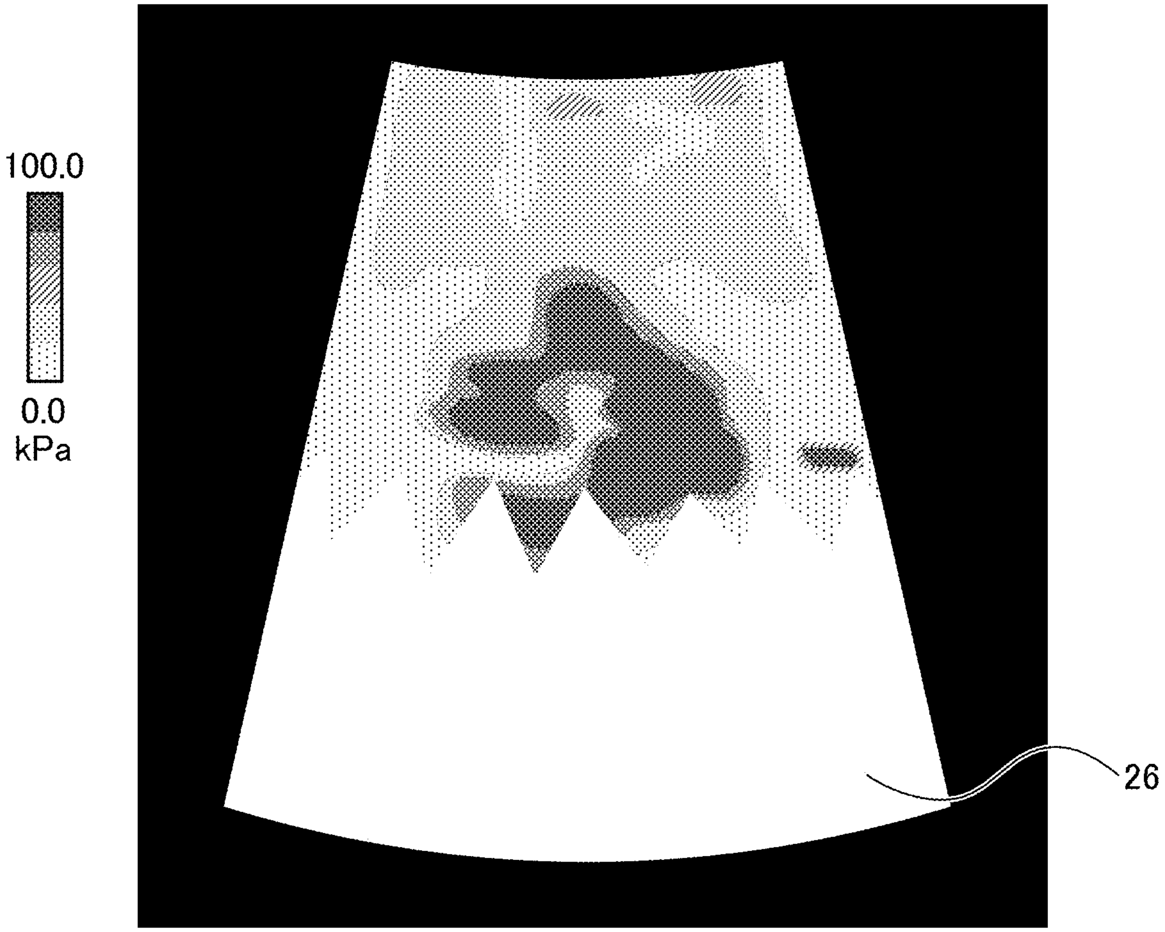
FIG. 17 is a diagram for explaining a hiding process.

For example, the image generator 140 performs the process of partially hiding ultrasonic image data. FIG. 17 is a diagram for explaining the hiding process. In FIG. 17, the process of partially hiding stiffness image data using the magnitude of displacement is described. In the example illustrated in FIG. 17, an area 26 in stiffness image data is white and displays nothing.

For example, the image generator 140 evaluates the reliability in three levels based on the magnitude of displacement at each point in the scan area. This evaluation may be made, for example, in the same manner as described in FIG. 16. For example, the image generator 140 determines that the upper area in the stiffness image data is "high", the area 25*a* is "medium", and the area 25*b* is "low".

The image generator 140 then generates stiffness image data only in the area determined to have "high" reliability and does not generate stiffness image data in the area 26 determined to have "medium" and "low" reliability. As described above, the image generator 140 does not generate stiffness image data corresponding to the area 26 thereby hiding the area 26.

As described above, the image generator 140 changes, for example, the pixel value of each point included in the stiffness image data using the magnitude of displacement at each point. Although the reliability is evaluated in three levels in the example above, the embodiments are not limited to this example. For example, the image generator 140 may evaluate the reliability in two levels by using a single threshold or may evaluate the reliability in multiple levels by using a plurality of thresholds.

Although the stiffness image data is modified using the magnitude of displacement in the description here, the embodiments are not limited thereto. That is, the pixel value at each point included in a variety of ultrasonic image data described above can be changed by using any one of parameters including the index value of stiffness, the arrival time of the shear wave, the magnitude of displacement, and the variance at each point.

The ultrasonic diagnosis apparatus 10 thereby can visualize information represented by a variety of parameters, such as the stiffness of living tissue and the reliability thereof, on another ultrasonic image data.

Evaluation of Various Parameters

For example, the ultrasonic diagnosis apparatus 10 may evaluate a variety of parameters at each point in the region of interest and display the evaluation result.

For example, the display controller 173 evaluates at least one of parameters including the index value of the stiffness of living tissue based on the shear wave, the arrival time, the magnitude of displacement, and the variance of the arrival times at each point in the region of interest and displays the evaluation result.

Figure 18:
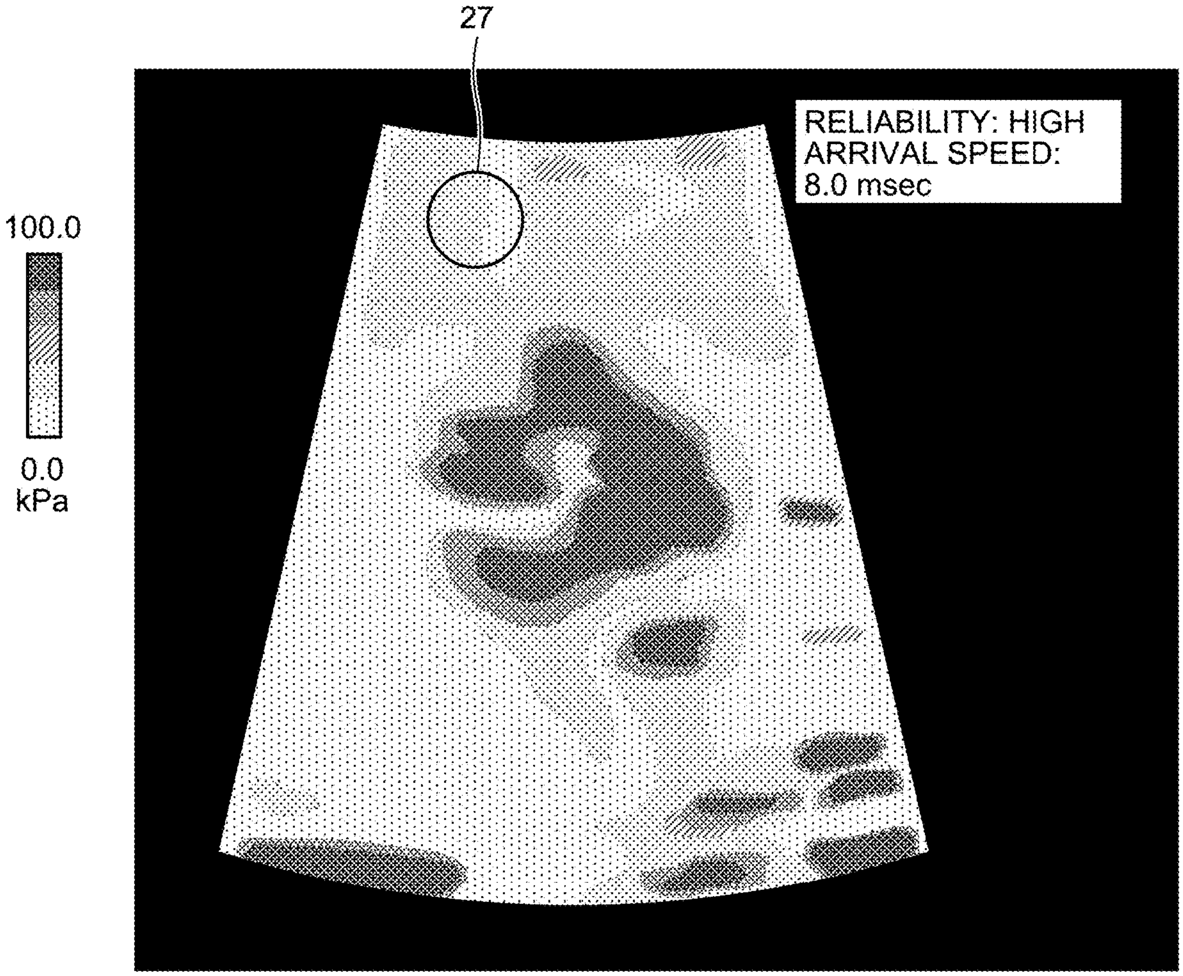
FIG. 18 is a diagram for explaining evaluation of a variety of parameters.

FIG. 18 is a diagram for explaining evaluation of a variety of parameters. FIG. 18 illustrates the stiffness image data in FIG. 2 and an ROI 27 designated on that image for reliability evaluation.

For example, the display controller 173 accepts the designation of the ROI 27 by the operator. The display controller 173 then evaluates a variety of parameters at each point in the accepted ROI 27.

As an example, the display controller 173 evaluates the reliability by comparing the variance at each point in the ROI 27 with a threshold. Specifically, the display controller 173 calculates the mean value of the variance at each point in the ROI 27. The display controller 173 then compares the calculated mean value with a threshold, determines that the reliability is "high" if the mean value is less than the threshold, and determines that the reliability is "low" if the mean value is equal to or greater than the threshold. For example, the display controller 173 causes the monitor 103 to display the evaluation result "reliability: high" as illustrated in FIG. 18.

It is noted that the example in FIG. 18 is given only by way of illustration. For example, the display controller 173 may make an evaluation by comparing not the mean value of the variance at each point in the ROI 27 but the maximum value of the variances in the ROI 27 with a threshold. Not only the evaluation result but also the parameter may be displayed per se on the monitor 103. For example, the display controller 173 calculates the mean value of the arrival time at each point in the ROI 27. The display controller 173 may display the calculated mean value "8.0 msec" on the monitor 103.

Display of Transmission Position of Push Pulse and Observation Direction

For example, the ultrasonic diagnosis apparatus 10 may display the transmission position of a push pulse and the observation direction.

Figure 19:
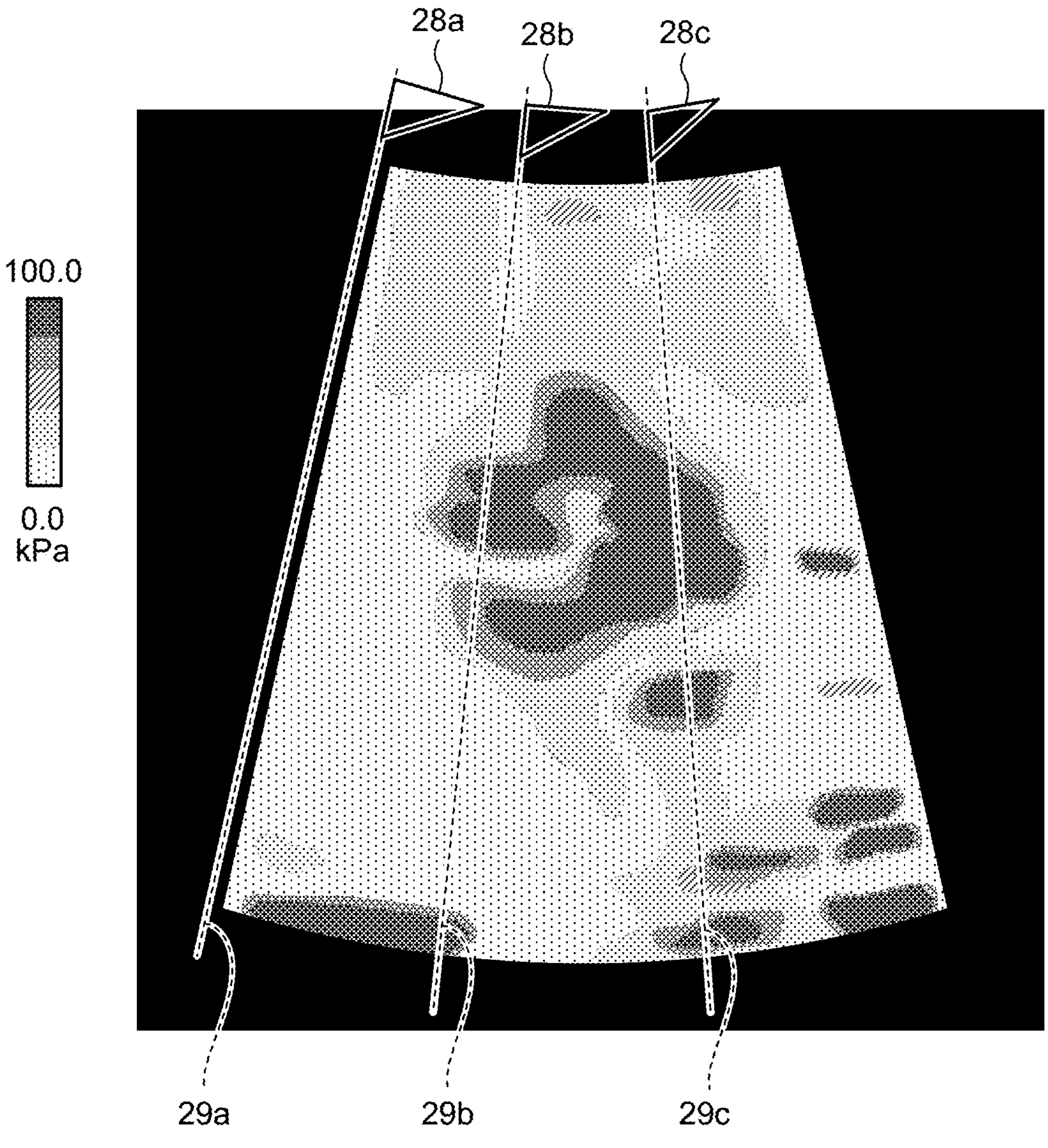
FIG. 19 is a diagram for explaining display of the transmission position of a push pulse and an observation direction.

FIG. 19 is a diagram for explaining display of the transmission position of a push pulse and the observation direction. FIG. 19 illustrates flags 28*a*, 28*b*, 28*c* and lines 29*a*,

29*b*, 29*c* on the stiffness image data in FIG. 2. In the example illustrated in FIG. 19 described below, a push pulse is transmitted on the lines 29*a*, 29*b*, 29*c*, and a shear wave propagating rightward from each transmission position is observed.

As illustrated in FIG. 19, the image generator 140 acquires information indicating the transmission position of a push pulse and the observation direction thereof from the transmission controller 171. The image generator 140 then generates the line 29*a* as image data corresponding to the transmission position of a push pulse at the left end. This line 29*a* is arranged at the transmission position of a push pulse at the left end. The image generator 140 also generates the flag 28*a* in order to indicate the observation direction of the push pulse at the left end. In this case, since the observation direction is on the right side of the transmission position of a push pulse, the image generator 140 arranges the flag 28*a* on the right side of the line 29*a*. Here, the image generator 140 lays the short side of the flag 28*a* on the line 29*a*. The flag 28*a* extending from the line 29*a* in the right direction explicitly shows that the shear wave propagating from the transmission position on the line 29*a* in the right direction is observed.

Parallel Display

For example, the ultrasonic diagnosis apparatus 10 may display a variety of ultrasonic image data described above together with scale marks (such as linear image data 20) superimposed thereon in parallel.

For example, the display controller 173 displays at least two pieces of image data in parallel, among the stiffness image data, the arrival time image data, the displacement image data, and the variance image data. The display controller 173 then superimposes at least one of the linear image data 20 based on the arrival times, the linear image data 22, the displacement position image data, and the linear image data 24, on at least one of the pieces of image data displayed in parallel.

Figure 20:
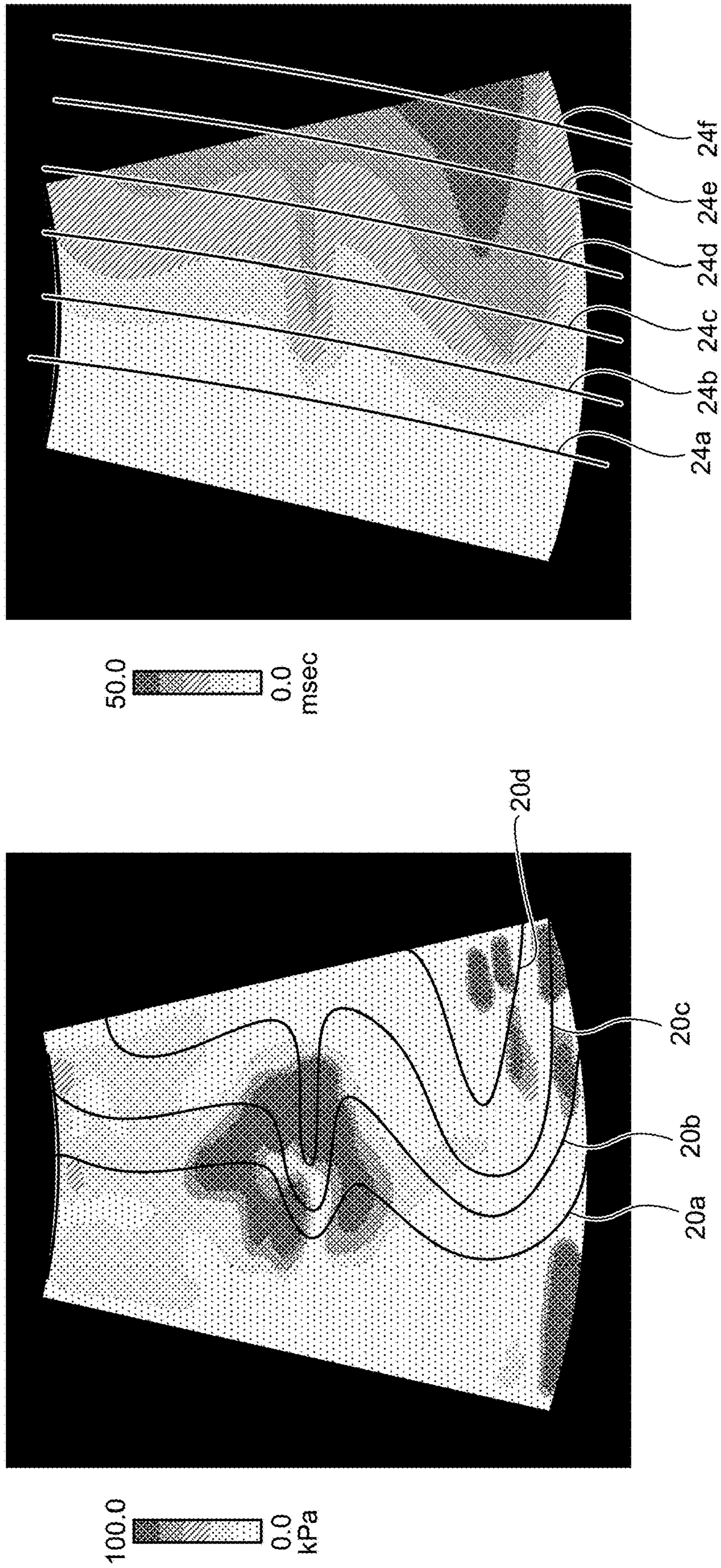
FIG. 20 is a diagram for explaining parallel display.

FIG. 20 is a diagram for explaining parallel display. FIG. 20 illustrates an image on the left side in which the linear image data 20 based on the arrival times is superimposed on the stiffness image data and illustrates an image on the right side in which the linear image data 24 is superimposed on the arrival time image data. It is noted that the image data illustrated here is merely an example and the display controller 173 may display a variety of ultrasonic image data and image data (for example, in FIGS. 16 and 17) modified with a variety of parameters, in parallel. The display controller 173 may superimpose any desired image data of the linear image data 20 of the arrival time, the linear image data 22, the displacement position image data, and the linear image data 24 described above. A variety of image data thus can be displayed in parallel.

Display of Linear Image Data 20 as Moving Image

For example, the ultrasonic diagnosis apparatus 10 may display linear image data 20 as a moving image.

For example, the image generator 140 generates a plurality of pieces of linear image data 20 based on the arrival times, for each of a plurality of different arrival times. The display controller 173 then displays the pieces of linear image data 20 in order from the earlier arrival time. The ultrasonic diagnosis apparatus 10 thus displays linear image data 20 as a moving image.

The ultrasonic diagnosis apparatus 10 can display the linear image data 22, the displacement position image data, and the linear image data 24 described above as a moving image in the same manner.

Calculation of Unique Parameter as Index of Reliability

In the embodiments described above, at least one of the arrival time, the magnitude of displacement (maximum amount of displacement), and the variance of the arrival times is imaged and displayed as an index of the reliability of stiffness. However, the embodiments are not limited thereto. For example, a unique parameter serving as an index of reliability can be calculated by combining a plurality of parameters out of the above parameters serving as indices of reliability of stiffness.

For example, the calculator 174 calculates a value based on the magnitude of displacement and the variance, as an index of reliability of stiffness. Here, the magnitude of displacement is, for example, the maximum amount of displacement, and the greater is this value, the higher is the reliability. On the other hand, the greater is the variance, the lower is the reliability. For example, the calculator 174 calculates a unique parameter serving as an index of reliability by scoring the maximum amount of displacement and the reciprocal of the variance.

The linear image generator 172 and the image generator 140 then execute the process explained in the foregoing embodiments using the calculated unique parameter in place of the arrival time, the magnitude of displacement, or the variance of the arrival times. For example, the linear image generator 172 assigns a pixel value corresponding to the unique parameter to each position included in the linear image data 20. For example, the image generator 140 generates, as a background image, image data in which the pixel value corresponding to the unique parameter is assigned to each position in the scan area. For example, the image generator 140 changes a pixel value at each position included in the background image in accordance with the unique parameter at each position in the scan area.

The embodiments are not limited to the example above. The calculator 174 may calculate a unique parameter serving as an index of reliability by combining any number of any of the parameters including the arrival time, the magnitude of displacement (maximum amount of displacement), and the variance of the arrival times.

Linked Reliability Display in Parallel Display

In the parallel display described above, the reliability display in images to be displayed in parallel may be linked with each other. That is, in parallel display, if the parameter (for example, the arrival time, the magnitude of displacement, the variance, and the unique parameter) serving as an index of reliability at each position included in stiffness image data does not satisfy a predetermined condition, the display controller 173 hides the image at that position and hides the image corresponding to that position in the linear image data 20 to be displayed in parallel.

Figure 21:
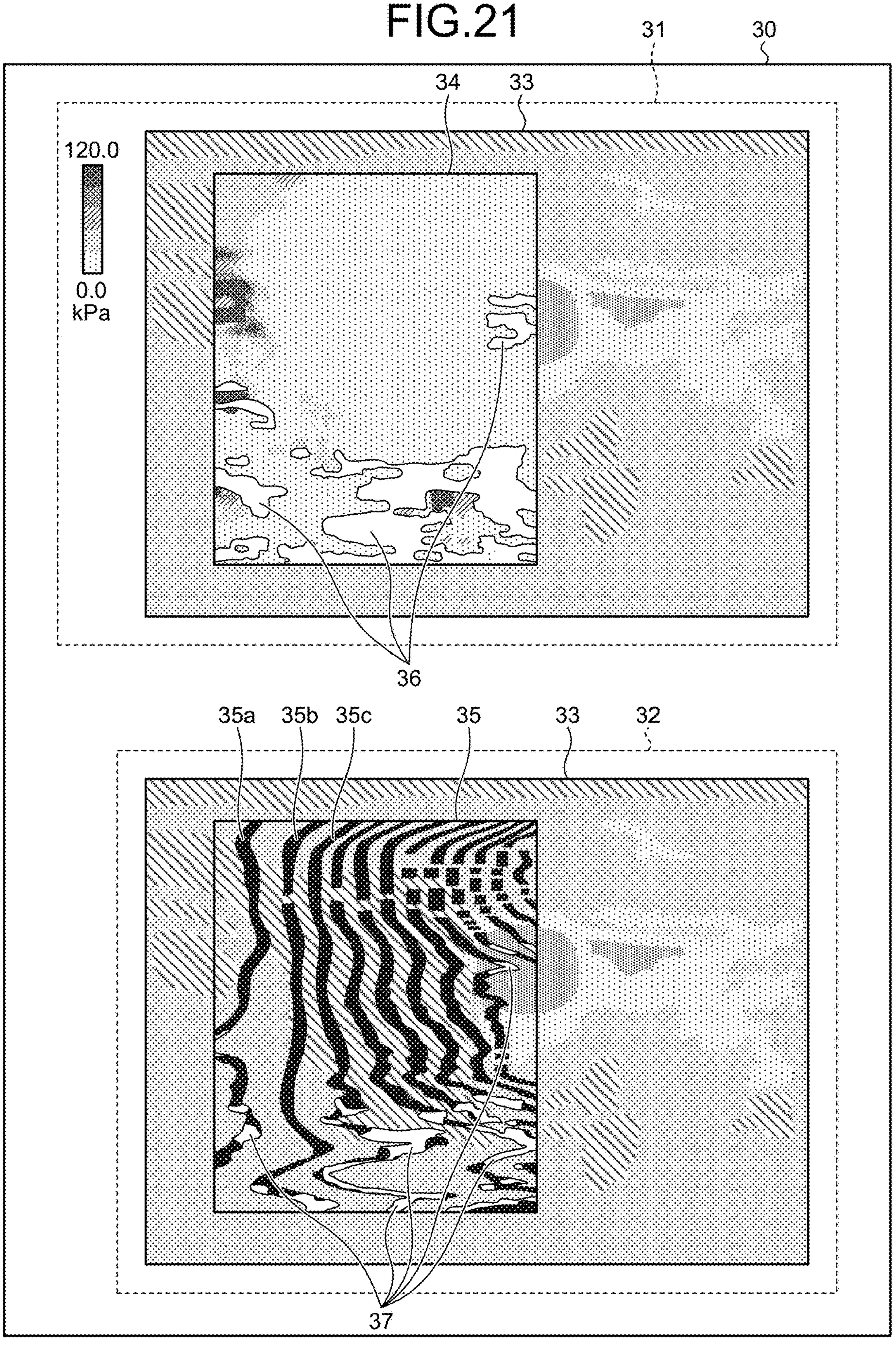
FIG. 21 is a diagram illustrating an example of a display image appearing on a monitor during parallel display.

FIG. 21 is a diagram illustrating an example of a display image 30 appearing on the monitor during parallel display. The display image 30 includes a superimposed image 31 and a superimposed image 32. The superimposed image 31 and the superimposed image 32 are an image in which a stiffness image 34 or a linear image group 35 is superimposed on a B mode image 33 generated based on the reflected-wave data in a certain scan area. That is, the stiffness image 34 represents the stiffness in the corresponding area in the B mode image 33. The linear image group 35 includes a plurality of linear images such as linear images 35*a*, 35*b*, 35*c* . . . and is generated based on the arrival times in the corresponding area in the B mode image 33.

Here, in the stiffness image 34, an area 36 with low reliability is hidden. In the example in FIG. 21, the area 36 is shown as a white area surrounded by a black line. For example, the display controller 173 hides the area 36 by changing the pixel value at a point at which the variance is equal to or greater than a predetermined threshold, among the points included in the stiffness image 34. Although the area 36 is shown as a white area surrounded by a black line, the embodiments are not limited thereto. For example, the area 36 may be shown as a black area or may be shown as a colorless area. When the area 36 is shown as a colorless area, the B mode image 33 as a background is displayed as it is.

In FIG. 21, in the linear image group 35, an area 37 corresponding to the area 36 is displayed in a color different from other areas. In the example in FIG. 21, the area 37 is shown as a white area surrounded by a black line. For example, the display controller 173 displays the area 37 in a color different from other areas by changing the pixel value at a point at which the variance is equal to or greater than a predetermined threshold, among the points included in the linear image group 35.

As described above, when performing parallel display, the display controller 173 changes each of a plurality of images to be displayed in parallel, using the same threshold for the index value of reliability. The display controller 173 thereby can hide a plurality of images to be displayed in parallel in such a manner that they are linked to each other.

Although FIG. 21 illustrates an example in which the area 36 is shown as a white area surrounded by a black line, the embodiments are not limited to this example. For example, the area 36 may be shown as a black area or may be shown as a colorless area. When the area 36 is shown as a colorless area, the B mode image 33 used as a background is displayed as it is. In FIG. 21 described above, the variance is used as an index value of reliability. However, the embodiments are not limited thereto. For example, any of the parameters including the arrival time, the magnitude of displacement, the variance, and the unique parameter may be used as a parameter serving as an index of reliability.

It is noted that the components of each device illustrated in the description of the foregoing embodiments are functional concepts and may not necessarily be physically configured as illustrated in the drawings. That is, specific manners of distribution and integration of the devices are not limited to those illustrated in the drawings and the whole or part thereof may be distributed or integrated functionally or physically in any units depending on various loads and use conditions. The whole or any part of the processing functions in each device may be implemented by a CPU and a computer program that is analyzed and executed by the CPU, or may be implemented by hardware with wired logic.

Each process to be performed by the ultrasonic diagnosis apparatus 10 described in the foregoing embodiments can be implemented by executing an image processing program prepared in advance. The image processing program can be distributed over networks such as the Internet. Otherwise, the image processing program may be recorded on a non-transitory computer-readable recording medium such as a hard disk, a flexible disk (FD), a compact disc read only memory (CD-ROM), a magnetooptical disc (MO), and a digital versatile disc (DVD) and read out from the non-transitory recording medium by a computer for execution.

At least one of the embodiments described above can represent the reliability of the stiffness of living tissue on an ultrasonic image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnosis apparatus, comprising:
a processing circuit configured to:
transmit, via an ultrasonic probe, a displacement-producing ultrasonic wave for causing displacement in living tissue based on acoustic radiation force;
transmit, via the ultrasonic probe, an observation ultrasonic wave for observing displacement of living tissue in a predetermined scan area, the displacement including a displacement caused by propagation of a shear wave generated based on the displacement-producing ultrasonic wave;
generate reflected-wave data based on a reflected wave received by the ultrasonic probe;
calculate, based on the reflected wave data, a reliability index value including a reliability of a parameter based on a shear wave for each of a plurality of positions in the predetermined scan area;
generate image data in which a pixel value corresponding to the calculated reliability index value is assigned to each position in the scan area; and
display, on a display device, a composite image in which an image generated based on the image data is superimposed on a medical image corresponding to a region including the scan area.

2. The ultrasonic diagnosis apparatus according to claim 1, wherein the processing circuit is further configured to calculate, for each of the plurality of positions in the scan area, a variance value of arrival times at which the shear wave reaches each position, based on the displacement over a plurality of time phases as the reliability index value, and generate the image data in which a pixel value corresponding to the reliability index value is assigned to each position.

3. The ultrasonic diagnosis apparatus according to claim 1, wherein the processing circuitry is further configured to:
determine, for each of the plurality of positions in the scan area, a time phase at which the shear wave arrives, based on the displacement over a plurality of time phases,
calculate, as the reliability index value, at least one of (i) a variance value of the determined time phase, and (ii) a value based on the variance value and a magnitude of the displacement, and
generate image data in which a pixel value corresponding to the reliability index value is assigned to each position.

4. The ultrasonic diagnosis apparatus according to claim 1, wherein the processing circuit is further configured to:
calculate, as the reliability index value, an index value representing a reliability of stiffness of living tissue based on the shear wave for each of the plurality of positions in the scan area, and
generate image data in which a pixel value corresponding to the reliability index value is assigned to each position.

5. The ultrasonic diagnosis apparatus according to claim 1, wherein the processing circuit is further configured to:
calculate, for each of the plurality of positions in the scan area, an index value representing stiffness of living tissue based on the shear wave, generate second image data in which a pixel value corresponding to the stiffness index value is assigned to each position, and display, on the medical image, a second image generated based on the second image data.

6. The ultrasonic diagnosis apparatus according to claim 1, wherein the processing circuit is further configured to:

calculate, for each of the plurality of positions in the scan area, an index value representing a displacement amount of tissue caused by propagation of the shear wave, generate third image data in which a pixel value corresponding to the displacement amount is assigned to each position, and display, on the medical image, a third image generated based on the third image data.

7. The ultrasonic diagnosis apparatus according to claim 1, wherein the processing circuit is further configured to:

calculate, for each of the plurality of positions in the scan area, an index value representing an arrival time of the shear wave, generate fourth image data in which a pixel value corresponding to the arrival times is assigned to each position, and display, on the medical image, a fourth image generated based on the fourth image data.

8. The ultrasonic diagnosis apparatus according to claim 1, wherein the processing circuit is further configured to generate, as the medical image, an image based on at least one of:

fifth image data in which a pixel value corresponding to B-mode signal intensity is assigned to each position in the scan area;

sixth image data in which a pixel value corresponding to an index value representing stiffness of living tissue based on a shear wave is assigned to each position in the scan area;

seventh image data in which a pixel value corresponding to a specific time phase at each position is assigned;

eighth image data in which a pixel value corresponding to a magnitude of displacement at each position is assigned;

ninth image data in which a pixel value corresponding to a variance of the specific time phases at each position is assigned; and tenth image data in which a pixel value corresponding to a value based on the variance of the specific time phase and the magnitude of the displacement at each position is assigned.

9. The ultrasonic diagnosis apparatus according to claim 8, wherein the processing circuit is further configured to change a pixel value at each position in the medical image using any one of parameters including the stiffness index value, the specific time phase, the displacement magnitude, the variance, and the value based on the variance and the displacement magnitude.

10. The ultrasonic diagnosis apparatus according to claim 8, wherein the processing circuit is further configured to display, in parallel, images based on at least two pieces of image data selected from the fifth image data, the sixth image data, the seventh image data, the eighth image data, the ninth image data, and the tenth image data, and superimposes an image generated based on the image data generated by the processing circuit onto at least one of the images displayed in parallel.

11. The ultrasonic diagnosis apparatus according to claim 10, wherein, in the parallel display, when any parameter selected from the specific time phase, the displacement magnitude, the variance, and the value based on the variance included in the sixth image data does not satisfy a predetermined condition, the processing circuit is configured to hide an image at the corresponding position, and hide an image corresponding to the position in the image data generated by the processing circuit to be displayed in parallel, and when any of the parameters satisfies the predetermined condition, the processing circuit is configured to display the image at the position, and display the corresponding image in the image data generated by the processing circuit.

12. The ultrasonic diagnosis apparatus according to claim 1, wherein the processing circuit is further configured to evaluate at least one of parameters including an index value representing stiffness of living tissue based on a shear wave, the specific time phase, the displacement magnitude, a variance of the specific time phases, and a value based on the variance and the displacement magnitude for each position in a region of interest and displays an evaluation result.

13. The ultrasonic diagnosis apparatus according to claim 1, wherein the processing circuit is further configured to calculate displacement over a plurality of time phases for each of the plurality of positions in the scan area, calculate the reliability index value by combining a plurality of index values including a reliability of stiffness based on the shear wave, and generate image data in which a pixel value corresponding to the reliability of stiffness is assigned to each position.

14. The ultrasonic diagnosis apparatus according to claim 1, wherein the processing circuit is further configured to set a region of interest in the composite image for evaluating at least one of a shear wave based parameter and the reliability index value included in the image generated based on the image data.

15. The ultrasonic diagnosis apparatus according to claim 14, wherein the processing circuit is further configured to calculate an average value of at least one of the shear wave based parameter and the reliability index value in the region of interest.

16. The ultrasonic diagnosis apparatus according to claim 15, wherein the processing circuit is further configured to evaluate reliability in the region of interest based on the calculated average value and a threshold, and display information representing the evaluation result on the display device.

17. The ultrasonic diagnosis apparatus according to claim 1, wherein the processing circuit is further configured to generate, as first image data, the image data in which pixel values corresponding to the reliability index values are assigned to each position in the scan area, generate, as second image data, image data in which pixel values corresponding to stiffness index values based on the shear wave are assigned to each position, display a first composite image in which a first image based on the first image data is superimposed on the medical image, and display a second composite image in which a second image based on the second image data is superimposed on the medical image.

18. The ultrasonic diagnosis apparatus according to claim 1, wherein the processing circuit is further configured to generate, as first image data, the image data in which pixel values corresponding to the reliability index values are assigned to each position in the scan area, generate, as third image data, image data in which pixel values corresponding to displacement amounts caused by propagation of the shear wave are assigned to each position, display a first composite image in which a first image based on the first image data is superimposed on the medical image, and display a third composite image in which a third image based on the third image data is superimposed on the medical image.

19. The ultrasonic diagnosis apparatus according to claim 1, wherein the processing circuit is further configured to generate, as first image data, the image data in which pixel values corresponding to the reliability index values are assigned to each position in the scan area, generates, as fourth image data, image data in which pixel values corresponding to arrival times of the shear wave are assigned to each position, display a first composite image in which a first image based on the first image data is superimposed on the medical image, and display a fourth composite image in which a fourth image based on the fourth image data is superimposed on the medical image.

* * * * *